(12) United States Patent
Bang et al.

(10) Patent No.: US 10,695,032 B2
(45) Date of Patent: Jun. 30, 2020

(54) MEDICAL IMAGE DISPLAY APPARATUS AND METHOD THEREFOR

(71) Applicant: SAMSUNG ELECTRONICS CO., LTD., Suwon-si (KR)

(72) Inventors: Won-chul Bang, Seongnam-si (KR); Ji-won Ryu, Seoul (KR); Young-taek Oh, Hanam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 115 days.

(21) Appl. No.: 15/836,076

(22) Filed: Dec. 8, 2017

(65) Prior Publication Data

US 2018/0161012 A1    Jun. 14, 2018

(30) Foreign Application Priority Data

Dec. 9, 2016    (KR) ........................ 10-2016-0168002

(51) Int. Cl.
*A61B 8/08* (2006.01)
*A61B 8/00* (2006.01)
(Continued)

(52) U.S. Cl.
CPC .............. *A61B 8/52* (2013.01); *A61B 6/4417* (2013.01); *A61B 6/5247* (2013.01); *A61B 8/085* (2013.01);
(Continued)

(58) Field of Classification Search
CPC ......... A61B 8/52; A61B 34/20; A61B 6/4417; A61B 6/5247
See application file for complete search history.

(56) References Cited

U.S. PATENT DOCUMENTS 8,369,592 B2    2/2013    Leroy et al.
8,447,384 B2    5/2013    Xu et al.
(Continued)

FOREIGN PATENT DOCUMENTS

JP    2010-172701 A    8/2010
JP    2011-11001 A    1/2011
(Continued)

OTHER PUBLICATIONS

Communication dated Dec. 14, 2017 by the Korean Intellectual Property Office in counterpart Korean Patent Application No. 10-2016-0168002.
(Continued)

*Primary Examiner* — Mekonen T Bekele
*Assistant Examiner* — Molly Delaney
(74) *Attorney, Agent, or Firm* — Sughrue Mion, PLLC

(57) ABSTRACT

A medical image display apparatus for displaying a medical image generated from first medical image data obtained from an object by a probe, including at least one processor configured to obtain information about a position at which tissue from the object is extracted by a needle, based on a signal received from a sensor attached to at least one from among the probe and the needle, and locate a tissue extraction position in the first medical image data based on the information, and a display configured to display a first medical image on which the tissue extraction position is marked, the first medical image being generated from the first medical image data.

20 Claims, 18 Drawing Sheets

(51) Int. Cl.
*A61B 6/00* (2006.01)
*A61B 17/34* (2006.01)
*A61B 8/14* (2006.01)
*G06T 7/00* (2017.01)
*A61B 34/20* (2016.01)
*A61B 90/00* (2016.01)
*A61B 50/13* (2016.01)
*A61B 17/00* (2006.01)
*A61B 34/00* (2016.01)
*A61B 34/10* (2016.01)
*A61B 10/02* (2006.01)

(52) U.S. Cl.
CPC .............. *A61B 8/0841* (2013.01); *A61B 8/14* (2013.01); *A61B 8/4245* (2013.01); *A61B 8/463* (2013.01); *A61B 8/5238* (2013.01); *A61B 8/5261* (2013.01); *A61B 17/3403* (2013.01); *G06T 7/0012* (2013.01); *A61B 8/467* (2013.01); *A61B 10/0233* (2013.01); *A61B 34/25* (2016.02); *A61B 50/13* (2016.02); *A61B 2017/00274* (2013.01); *A61B 2017/3413* (2013.01); *A61B 2034/105* (2016.02); *A61B 2034/2051* (2016.02); *A61B 2090/378* (2016.02)

(56) References Cited

U.S. PATENT DOCUMENTS

| | | |
|---|---|---|
| 9,498,185 B2 | 11/2016 | Kimoto et al. |
| 2010/0204579 A1* | 8/2010 | Yoshida ............... A61B 8/0833 600/443 |
| 2010/0298704 A1* | 11/2010 | Pelissier .............. A61B 8/0833 600/443 |
| 2011/0082363 A1 | 4/2011 | Xu et al. |
| 2011/0130685 A1 | 6/2011 | Sarvazyan et al. |
| 2012/0022546 A1* | 1/2012 | Hubschman ........ A61F 9/00736 606/107 |
| 2012/0078103 A1* | 3/2012 | Tashiro ................ A61B 8/0841 600/443 |
| 2012/0089008 A1* | 4/2012 | Strehl .................. G01R 33/286 600/411 |
| 2012/0302873 A1* | 11/2012 | Tajima ................... A61B 6/025 600/424 |
| 2015/0208948 A1 | 7/2015 | Wei et al. |
| 2016/0022247 A1 | 1/2016 | Jin et al. |
| 2016/0066887 A1 | 3/2016 | Hyun et al. |
| 2017/0095226 A1* | 4/2017 | Tanaka ............... A61B 17/3403 |
| 2017/0164931 A1* | 6/2017 | Ng ....................... A61B 8/0841 |

FOREIGN PATENT DOCUMENTS

| | | |
|---|---|---|
| JP | 2011-524772 A | 9/2011 |
| JP | 5842810 B2 | 1/2016 |
| KR | 10-2016-0012590 A | 2/2016 |
| WO | 2013/085139 A1 | 6/2013 |
| WO | 2015/136392 A1 | 9/2015 |

OTHER PUBLICATIONS

Communication dated May 16, 2018, from the European Patent Office in counterpart European Application No. 17204611.2.
Communication dated Jun. 28, 2018, issued by the Korean Intellectual Property Office in corresponding Korean Application No. 10-2016-0168002.
Communication dated Sep. 30, 2019, issued by the European Patent Office in counterpart European Application No. 17204611.2.

* cited by examiner

MEDICAL IMAGE DISPLAY APPARATUS AND METHOD THEREFOR

CROSS-REFERENCE TO RELATED APPLICATION

This application claims benefit from Korean Patent Application No. 10-2016-0168002, filed on Dec. 9, 2016, in the Korean Intellectual Property Office, the disclosure of which is incorporated herein by reference in its entirety.

BACKGROUND

1. Field

Exemplary embodiments consistent with the present disclosure relate to methods and apparatuses for displaying a medical image, and more particularly, to methods and apparatuses for automatically determining and marking a position at which a biopsy is performed to extract tissue from an object.

2. Description of Related Art

Ultrasound image obtaining apparatuses transmit ultrasound signals generated by transducers of an ultrasound probe to a part inside an object, and receive information regarding echo signals reflected from the part inside the object, thereby obtaining at least one image of the part inside the object. In particular, ultrasound image obtaining apparatuses are used for medical purposes, including observation of the interior of an object, detection of foreign substances, determination of lesions of the object, diagnosis of damage to the object, or the like.

Such ultrasound image obtaining apparatuses provide high stability, display images in real time, and are safe in comparison to X-ray image obtaining apparatuses due to the lack of radioactive exposure. Therefore, ultrasound image obtaining apparatuses are widely used together with other image obtaining apparatuses.

A biopsy is a medical test performed to extract tissue for a pathological examination by inserting a hollow needle into an internal organ of the object without cutting skin. When a biopsy is performed, ultrasound image obtaining apparatuses may be used because ultrasound image obtaining apparatuses may display an image in real time. A user may check a lesion by touching the skin of a patient with an ultrasound probe, may insert a needle into the lesion while checking an ultrasound image in real time, and thus may obtain tissue of the lesion.

In this regard, in order to precisely obtain tissue of the lesion, an accurate image of an internal part of the object has to be provided. Thus, there is a demand for medical image obtaining apparatuses capable of displaying an ultrasound image having a low signal-to-noise ratio along with an image such as a magnetic resonance (MR) image or a computed tomography (CT) image having a high signal-to-noise ratio and obtained by using a different medical image obtaining method.

SUMMARY

Provided are a medical image display apparatus and method therefor which automatically determine and mark a position at which a biopsy is performed.

Provided are a medical image displaying apparatus and method therefor which automatically record biopsy positions relative to a reference point in order to compare the positions in an object on which biopsies are performed at different times.

Additional aspects will be set forth in part in the description which follows and, in part, will be apparent from the description, or may be learned by practice of the presented exemplary embodiments.

According to an aspect of an exemplary embodiment, a medical image display apparatus for displaying a medical image generated from first medical image data obtained from an object by a probe includes at least one processor configured to obtain information about a position at which tissue from the object is extracted by a needle, based on a signal received from a sensor attached to at least one from among the probe and the needle, and locate a tissue extraction position in the first medical image data based on the information, and a display configured to display a first medical image on which the tissue extraction position is marked, the first medical image being generated from the first medical image data.

The at least one processor may be further configured to locate the tissue extraction position in second medical image data corresponding to the object, based on the information, the display may be configured to further display a second medical image on which the tissue extraction position is marked, the second medical image being generated from the second medical image data, and the second medical image data may include at least one of magnetic resonance (MR) image data, computed tomography (CT) image data, and model image data obtained by modeling the object.

The at least one processor may be further configured to obtain information about a position of the needle based on the signal received from the sensor attached to the at least one of the probe and the needle, match the position of the needle with the second medical image data, and locate the tissue extraction position in the second medical image data, based on a result of the matching.

The at least one processor may be further configured to obtain information about a first position of the needle before the tissue is extracted from the object by the needle, obtain information about a second position of the needle at which the tissue is extracted from the object by the needle, and determine the tissue extraction position to correspond to the second position in the second medical image data, based on a reference point corresponding to the first position in the second medical image data.

The medical image display apparatus may further include an input interface, and the at least one processor may be further configured to obtain the information about the first position of the needle upon receipt of a user input through the input interface, and match the first position of the needle with the reference point in the second medical image data.

The reference point may be determined based on at least one from among pre-stored information or a user input.

The at least one processor may be further configured to obtain, as the information about the second position, coordinate information corresponding to the second position in a coordinate system including the first position as a starting point, and determine the tissue extraction position with respect to the reference point, based on the coordinate information.

The medical image display apparatus may further include an input interface, the information about the first position and the information about the second position may be obtained by a position sensor included in the probe, the needle may be attached to the probe, and the at least one processor may be further configured to obtain information about a position of the probe, upon receipt of a user input via the input interface, and determine the information about the second position based on at least one of a distance which the needle has moved with respect to the probe and a direction in which the needle has moved with respect to the probe.

The medical image display apparatus may further include a storage configured to store third medical image data corresponding to a biopsy that was previously performed on the object, the third medical image data including information about a previous reference point and a previous tissue extraction position, and the at least one processor may be further configured to obtain the third medical image data from the storage, match the second medical image data with the third medical image data by matching a reference point of the second medical image data with the previous reference point of the third medical image data, generate, from the second medical image data, a second medical image on which the tissue extraction position is marked, and generate, from the third medical image data, a third medical image on which the previous tissue extraction position is marked, wherein the third medical image includes a cross-section of the object which corresponds to the second medical image, and the display may be further configured to display the second medical image and the third medical image.

The medical image display apparatus may further include a storage configured to store, as the information about the second position, coordinate information corresponding to the second position in a coordinate system including the first position as a starting point.

According to another aspect of an exemplary embodiment, a method of displaying a medical image generated from first medical image data obtained from an object by a probe includes obtaining information about a position at which tissue from the object is extracted by a needle, based on a signal received from a sensor attached to at least one from among the probe and the needle, locating a tissue extraction position in the first medical image data based on the information, and displaying a first medical image on which the tissue extraction position is marked, the first medical image being generated from the first medical image data.

The method may further include locating the tissue extraction position in second medical image data corresponding to the object, based on the information, and displaying a second medical image on which the tissue extraction position is marked, the second medical image being generated from the second medical image data, wherein the second medical image data comprises at least one of magnetic resonance (MR) image data, computed tomography (CT) image data, and model image data obtained by modeling the object.

The obtaining of the information about the position may include obtaining information about a position of the needle based on the signal received from the sensor attached to at least one of the probe and the needle, and the determining of the tissue extraction position may includes matching the position of the needle with the second medical image data, and locating the tissue extraction position in the second medical image data, based on a result of the matching.

The obtaining of the information about the position may include obtaining information about a first position of the needle before the tissue is extracted from the object by the needle, and obtaining information about a second position of the needle at which the tissue is extracted from the object by the needle, and the determining of the tissue extraction position in the second medical image data may include determining the tissue extraction position to correspond to the second position in the second medical image data, based on a reference point corresponding to the first position in the second medical image data.

The information about the first position of the needle may be obtained when a user input is received, and the locating of the tissue extraction position in the second medical image data may include matching a position of the needle with the second medical image data by matching the first position of the needle with the reference point in the second medical image data.

The reference point may be determined based on at least one from among pre-stored information or a user input.

The obtaining of the information about the second position may include obtaining, as the information about the second position, coordinate information corresponding to the second position in a coordinate system including the first position as a starting point, and the locating of the tissue extraction position in the second medical image data may include determining the tissue extraction position with respect to the reference point, based on the coordinate information.

The information about the first position and the information about the second position may be obtained by a position sensor included in the probe, the needle may be attached to the probe, and the obtaining of the information about the second position may include obtaining, when a user input is received, information about a position of the probe to which the needle is attached, and determining the information about the second position based on at least one of a distance which the needle has moved with respect to the probe and a direction in which the needle has moved with respect to the probe.

The method may further include storing third medical image data in relation to a biopsy that was previously performed on the object, the third medical image data including information about a previous reference point and a previous tissue extraction position, and the displaying of the second medical image may include obtaining the stored third medical image data, matching the second medical image data with the third medical image data by matching a reference point of the second medical image data with the previous reference point of the third medical image data, generating, from the second medical image data, a second medical image on which the tissue extraction position is marked, generating, from the third medical image data, a third medical image on which the previous tissue extraction position is marked, wherein the third medical image includes a cross-section of the object which corresponds to the second medical image, and displaying the second medical image and the third medical image.

The method may further include storing, as the information about the second position, coordinate information corresponding to the second position in a coordinate system including the first position as a starting point.

According to another aspect of an exemplary embodiment, a computer-readable recording medium having recorded thereon instructions to perform a method of displaying a medical image generated from first medical image data obtained from an object by a probe includes obtaining information about a position at which tissue from the object is extracted by a needle, based on a signal received from a sensor attached to at least one from among the probe and the needle, locating a tissue extraction position in the first medical image data based on the information, and displaying a first medical image on which the tissue extraction position is marked, the first medical image being generated from the first medical image data.

According to another aspect of an exemplary embodiment, a method of displaying one or more medical images includes in response to receiving a first user input, determining a first position of a needle with respect to an object, the needle being attached to a probe configured to acquire first medical image data, in response to receiving a second user input indicating that tissue has been extracted from the object using the needle, determining a second position of the needle with respect to the object, locating a first tissue extraction position in the first medical image data based on the second position, displaying a first medical image on which the first tissue extraction position is marked, matching second medical image data with the first medical image data based on the first position, locating a second tissue extraction position in the second medical image data based on the second position, the second tissue extraction position corresponding to the first tissue extraction position, and displaying a second medical image on which the second tissue extraction position is marked.

The second position may be determined by measuring a movement of the needle with respect to the probe between the first user input and the second user input.

The second medical image data may be matched with the first medical image data by matching the first position with a reference position in the second medical image data.

BRIEF DESCRIPTION OF THE DRAWINGS

These and other aspects will become apparent and more readily appreciated from the following description of the exemplary embodiments, taken in conjunction with the accompanying drawings in which.

DETAILED DESCRIPTION

Figure 1:
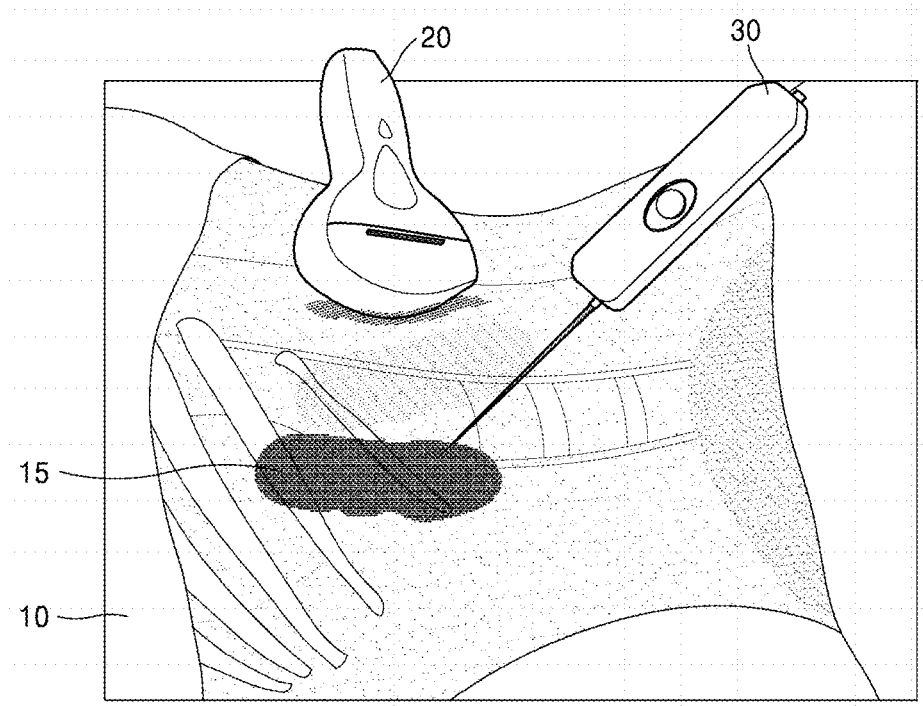
FIG. 1 is a diagram for describing a general biopsy, according to an exemplary embodiment.

Hereinafter, the present disclosure will now be described more fully with reference to the accompanying drawings, in which exemplary embodiments are shown. The present disclosure may, however, be embodied in many different forms and should not be construed as being limited to the exemplary embodiments set forth herein; rather, these exemplary embodiments are provided so that the present disclosure will be thorough and complete, and will fully convey the concept to one of ordinary skill in the art. In the drawings, for a more clear description of the present disclosure, parts or units that are not related to the present disclosure are omitted. Throughout the specification, like reference numerals in the drawings denote like elements.

The present disclosure may be described in terms of functional block components and various processing steps. Such functional blocks may be realized by any number of hardware and/or software components configured to perform the specified functions. For example, functional blocks of the present disclosure may be implemented by one or more microprocessors, or circuit configurations for specified functions. In addition, for example, functional blocks of the present disclosure may be implemented with various programming or scripting languages. Functional blocks may be implemented in algorithms that execute on one or more processors. Furthermore, the present disclosure could employ any number of conventional techniques for electronics configuration, signal processing, and/or data processing.

Furthermore, the connecting lines, or connectors shown in the various drawings presented are intended to represent exemplary functional relationships and/or physical or logical couplings between the various elements. It should be noted that many alternative or additional functional relationships, physical connections or logical connections may be present in a practical device.

Throughout the specification, a term "object" may be a target inanimated object or a target animated object, which is displayed via an image. Also, the object may be a whole or part of a human body and may include the liver, the heart, the womb, the brain, the breast, the abdominal part, or the like, a fetus, or a cross-section of a part of a human body.

Throughout the specification, a "user" may be, but is not limited to, a medical expert including a doctor, a nurse, a medical laboratory technologist, a sonographer, a medical image expert, or the like. Furthermore, throughout the specification, a term "medical image" may include, but is not limited to, an ultrasound image, a magnetic resonance (MR) image, an X-ray image, a computed tomography (CT)

image, a positron emission tomography (PET) image, and a model image obtained by modeling an object.

Throughout the specification, a term "medical image data" may refer to a data set capable of generating a medical image, and image data may include volume data and two-dimensional (2D) image data.

Hereinafter, the present disclosure will be described in detail by explaining exemplary embodiments of the disclosure with reference to the attached drawings in order to fully convey the concept of the disclosure to one of ordinary skill in the art.

As used herein, the term "and/or" includes any and all combinations of one or more of the associated listed items. Expressions such as "at least one of," when preceding a list of elements, modify the entire list of elements and do not modify the individual elements of the list.

FIG. 1 is a diagram for describing a general biopsy.

As illustrated in FIG. 1, a user may check a lesion 15 by touching a skin of a patient 10 with an ultrasound probe 20, may insert a needle 30 into the lesion 15 while checking an ultrasound image, and thus may obtain tissue. FIG. 1 illustrates a case in which the user performs the biopsy while separately moving the ultrasound probe 20 and the needle 30, but one or more exemplary embodiments are not limited thereto.

Figure 2A:
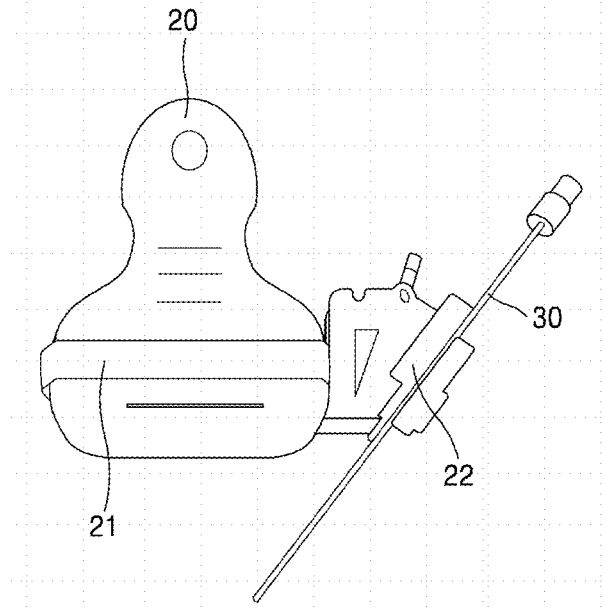
FIGS. 2A, 2B, and 2C illustrate examples of a probe and a needle used in a biopsy, according to an exemplary embodiment.
Figure 2B:
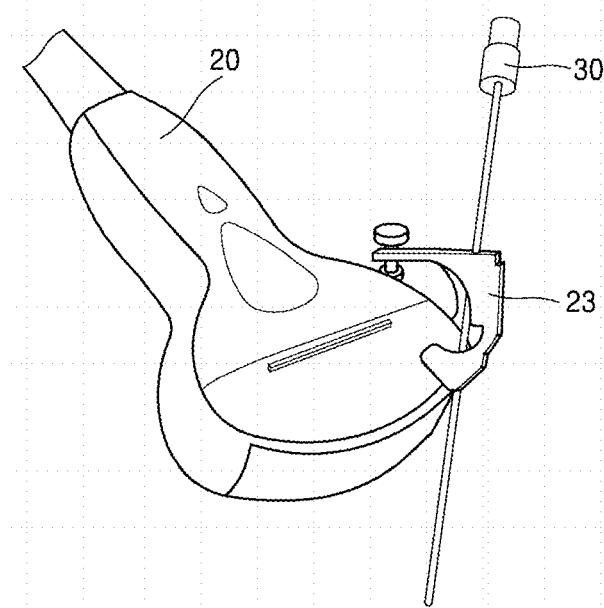
Figure 2C:
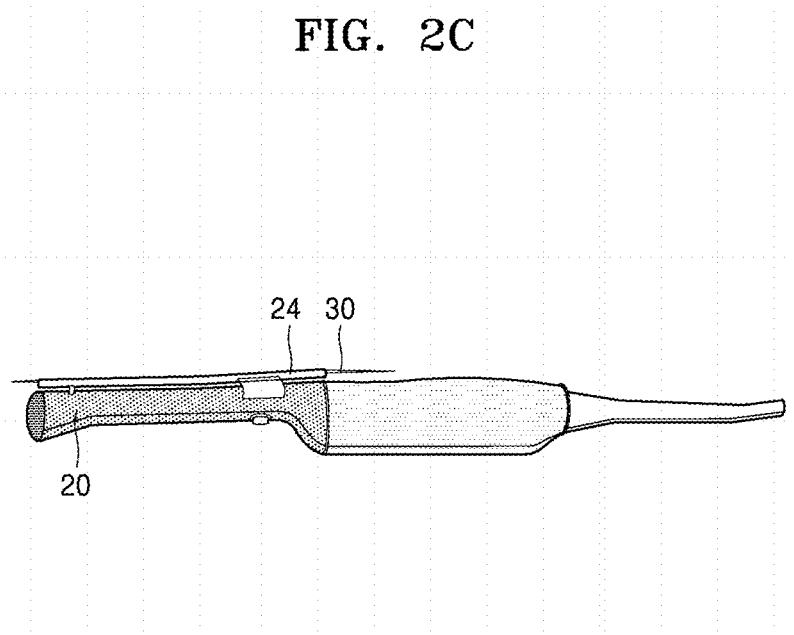

As illustrated in FIGS. 2A, 2B, and 2C, the ultrasound probe 20 to which the needle 30 is attached for a biopsy may be used.

FIGS. 2A and 2B illustrate an example of the ultrasound probe 20 that obtains an ultrasound image in an abdomen application, an OB/GYN application, or the like. The needle 30 may be attached to the ultrasound probe 20 in a manner that the needle 30 is located in a needle guide 22 on a bracket 21 fixed to an external surface of the ultrasound probe 20. The bracket 21 may be temporarily attached to the external surface of the ultrasound probe 20, and when a biopsy is not performed, the bracket 21 may be detached from the ultrasound probe 20.

FIG. 2B illustrates a needle guide 23 having a shape that is different from the needle guide 22 of FIG. 2A.

FIG. 2C illustrates an example of the ultrasound probe 20 that obtains an ultrasound image in an anus application or a vaginal application. The needle 30 may be attached to the ultrasound probe 20 in a manner that the needle 30 is located in a needle guide 24 fixed to an external surface of the ultrasound probe 20.

The ultrasound probe 20 is not limited to probes illustrated in FIGS. 2A, 2B, and 2C, and may include an ultrasound probe that obtains an ultrasound image in an abdomen application, an OB/GYN application, a vascular application, a cardiac application or the like. The needle guide 22, needle guide 24, and the bracket 21 which are fixed to the external surface of the ultrasound probe 20 are not limited to shapes illustrated in FIGS. 2A, 2B, and 2C, and may have various shapes capable of attaching the needle 30 to the ultrasound probe 20.

According to an exemplary embodiment, a biopsy may be performed by using the needle 30 attached to the ultrasound probe 20. For example, for ultrasonography with respect to a prostate, the ultrasound probe 20 of FIG. 2C may be inserted into a rectum via an anus, and the needle 30 may be inserted though an inner wall of the rectum in order to extract tissue with respect to a lesion to the prostate.

In this regard, a general ultrasound image display apparatus may compare a reference ultrasound image, which is obtained before a biopsy is performed, with an ultrasound image obtained while the biopsy is performed, and thus may display a trajectory of movement of a needle on the ultrasound image. A user may check a position at which the tissue was extracted by referring to the trajectory of the needle, and may manually mark the checked position.

In order to use at a later time the ultrasound image on which the tissue extraction position is marked, the general ultrasound image display apparatus may store the displayed ultrasound image and the marked position on the displayed ultrasound image. Ultrasound images that are displayed when a biopsy is performed may be ultrasound images of different cross-sections of an object. Thus, whenever a biopsy is performed, the general ultrasound image display apparatus stores marked positions on the ultrasound images of the different cross-sections of the object. Therefore, it was impossible to compare the ultrasound images stored in the general ultrasound image display apparatus and thus check a change in positions for biopsies performed at different times.

According to one or more exemplary embodiments, a medical image display apparatus and method therefor are provided to automatically record biopsy positions relative to a reference point in order to compare the positions in an object for biopsies performed at different times.

Figure 3A:
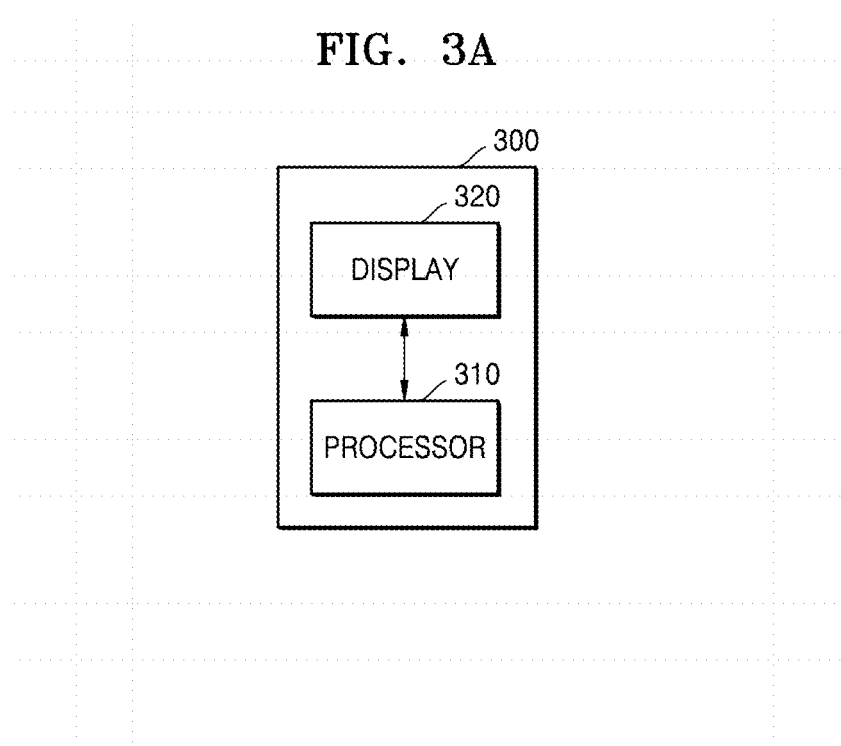
FIGS. 3A and 3B are block diagrams of a medical image display apparatus, according to an exemplary embodiment.
Figure 3B:
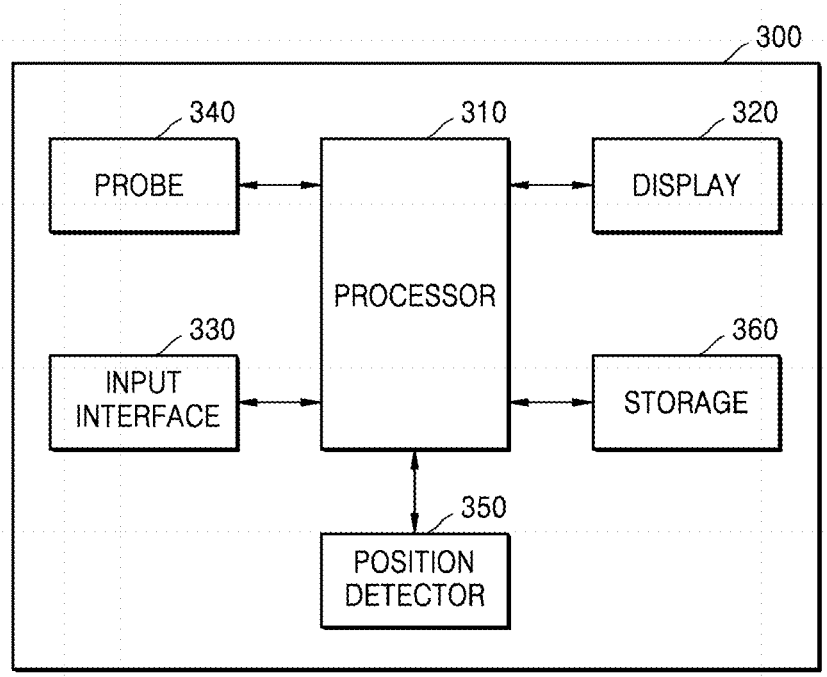

FIGS. 3A and 3B are block diagrams of a medical image display apparatus 300, according to an exemplary embodiment.

The medical image display apparatus 300 according to the present exemplary embodiment may be included in a diagnosis apparatus such as an ultrasound diagnosis apparatus or an endoscopy diagnosis apparatus, which is capable of obtaining and displaying a medical image. However, the present exemplary embodiment is not limited thereto, and the medical image display apparatus 300 may be an apparatus that does not directly obtain a medical image from an object but processes and displays a medical image obtained using a separate apparatus. In addition, the medical image display apparatus 300 may operate as a medical image obtaining apparatus or a medical image processing apparatus and a separate set-top box connected thereto in a wired or wireless manner.

The medical image display apparatus 300 may include a display 320 and a processor 310. While FIGS. 3A and 3B illustrate only one processor 310, the processor 310 may include any number of processors in exemplary embodiments.

According to the present exemplary embodiment, the processor 310 may control general operations of the medical image display apparatus 300, and may generate, from medical image data, a medical image on which a tissue extraction position is marked. The processor 310 may control the display 320 to display the generated medical image.

The processor 310 may obtain the medical image data of an object. The medical image data that the processor 310 uses to generate the medical image may be pre-stored data, data generated based on a signal received from the object in response to a signal transmitted to the object, or data received from an external apparatus or an external server.

The processor 310 may obtain the medical image data of the object. For example, the processor 310 may obtain at least one of ultrasound image data, MR image data, CT image data, and model image data obtained by modeling the object. However, the present exemplary embodiment is not limited thereto, and the processor 310 may obtain the medical image data that is obtained by using various methods. The processor 310 may obtain first medical image data obtained from the object via a probe. For example, the first medical image data may include the ultrasound image data.

The processor 310 may obtain information about a position in the object from which tissue is extracted by a needle, based on a signal received from a sensor attached to at least one of a probe and the needle. The processor 310 may determine or locate a tissue extraction position in the first medical image data, based on the obtained information.

The processor 310 may obtain second medical image data. For example, the second medical image data may include at least one of MR image data, CT image data, and model image data obtained by modeling the object. The processor 310 may determine or locate a tissue extraction position in the second medical image data, based on the obtained information.

According to the present exemplary embodiment, the information about a position in the object may be obtained by using a position sensor attached to the needle or a position sensor included in a probe. For example, the position sensor may include an electromagnetic (EM) sensor. If the position sensor is included in a probe to which a needle is attached, information about a position of the needle may be obtained based on information about a position of the probe. The medical image display apparatus 300 may determine a position at which tissue is extracted by the needle, based on at least one of a distance and a direction in which the needle has moved with respect to the probe in order to extract the tissue. The processor 310 may determine information about a tissue extraction position from the position of the probe, based on at least one of the distance and the direction in which the needle has moved with respect to the probe in order to extract the tissue. The distance in which the needle has moved with respect to the probe in order to extract the tissue may be a preset value or a user input value. When the medical image display apparatus 300 directly determines the position at which the tissue was extracted by the needle, by using the position sensor attached to the needle, an error may be decreased compared to a case in which the tissue extraction position is determined in consideration of a position of the needle relative to the probe.

The processor 310 may match the position of the needle with the medical image data. The processor 310 may determine the tissue extraction position in the medical image data, based on a result of the match.

The processor 310 may obtain information about a first position of the needle, as reference information with respect to a change in a position of the needle. The processor 310 may obtain the information about the first position of the needle before the tissue is extracted from the object by using the needle.

The processor 310 may match the first position of the needle with a reference point in the medical image data, thereby matching a position of the needle with the medical image data. The reference point in the medical image data may be determined based on pre-stored information or a user input.

According to the present exemplary embodiment, the processor 310 may obtain information about a second position in the object from which tissue is extracted by the needle. The processor 310 may obtain, as the information about the second position, coordinate information corresponding to the second position in a coordinate system including the first position as a starting point.

The processor 310 may determine a tissue extraction position corresponding to the second position in the medical image data, based on the reference point in the medical image data of the object, the reference point corresponding to the first position. The processor 310 may determine the tissue extraction position corresponding to the second position in the medical image data, based on a result of matching a position of the needle with the medical image data. The processor 310 may determine the tissue extraction position with respect to the reference point, based on the coordinate information corresponding to the second position with respect to the first position.

According to the present exemplary embodiment, the display 320 may display a first medical image on which the tissue extraction position is marked and that is generated from the first medical image data. For example, while a user prepares to perform a biopsy and then performs the biopsy, the display 320 may display a real-time ultrasound image generated from ultrasound image data. The display 320 may display a second medical image generated from the second medical image data. For example, the display 320 may display not only the real-time ultrasound image generated from ultrasound image data but may also display at least one of an MR image, a CT image, and a model image, so that a biopsy may be performed on an accurate position in the object. The display 320 may display the second medical image on which the tissue extraction position is marked and that is generated from the second medical image data.

The medical image display apparatus 300 is not limited to the exemplary embodiment of FIG. 3A. The medical image display apparatus 300 may include more elements than the elements shown in FIG. 3A. For example, as illustrated in FIG. 3B, the medical image display apparatus 300 according to the present exemplary embodiment may further include at least one of an input interface 330, a probe 340, a position detector 350, and a storage 360.

When a user input is received via the input interface 330, the processor 310 may obtain information about a position of the needle at a point of time when the user input is received.

For example, when the probe 340 to which a needle is attached is located on a reference part of an object, a user may input a user input, thereby recording, as a first position, a position of the needle at that point of time. In exemplary embodiments, probe 340 may be an ultrasound probe, and may for example correspond to ultrasound probe 20 of FIGS. 1, 2A, 2B, and 2C. Redundant descriptions thereof are omitted here.

When the user input is received via the input unit 330, the processor 310 may obtain information about the first position of the needle, and may match the first position of the needle with the reference point in the medical image data. The processor 310 may match a position of the needle with the medical image data by matching the first position of the needle with the reference point in the medical image data.

Furthermore, the user may input a user input before a biopsy is performed, during the biopsy, or after the biopsy is performed, so that the user may record, as a second position, a position of the needle at that point of time. The user input for recording the first position and the user input for recording the second position may be different from each other. For example, the user input for recording the first position may be a first input, and the user input for recording the second position may be a second input.

When the user input is received via the input unit 330, the processor 310 may obtain information about the second position of the needle. For example, when needle position information is obtained by a position sensor included in the probe 340, if the user input is received, the processor 310 may obtain information about a position of the probe 340 to which a needle is attached. The processor 310 may determine the information about the second position, based on at least one of a distance and a direction in which the needle has moved with respect to the probe 340 in order to extract tissue.

The position detector 350 may detect a position of at least one of the needle and the probe 340 to which the needle is attached. For example, an EM sensor may be installed inside or outside at least one of the needle and the probe 340 to which the needle is attached. The position detector 350 may sense a change in an electromagnetic field, thereby obtaining information about the position of at least one of the needle and the probe 340 to which the needle is attached. Alternatively, the position detector 350 may determine the position of at least one of the needle and the probe 340 to which the needle is attached, based on information received from a motion sensor included in at least one of the needle and the probe 340 to which the needle is attached. The motion sensor attached to the probe 340 will be described in detail below with reference to FIGS. 4A, 4B, and 4C. The position detector 350 may include a sensor included in or attached to at least one of the needle and the probe 340 to which the needle is attached.

According to the present exemplary embodiment, the storage 360 may store the medical image data including information about the reference point and the tissue extraction position. The storage 360 may store the information about the second position in the object from which the tissue is extracted by the needle. The storage 360 may store, as the information about the second position, the coordinate information corresponding to the second position of the needle in the coordinate system including the first position of the needle as the starting point.

The storage 360 may store third medical image data including a reference point and information about a previous tissue extraction position, which is related to a biopsy that was previously performed on the object. The processor 310 may obtain the third medical image data from the storage 360.

The processor 310 may match the reference point in the second medical image data with the reference point in the third medical image data, thereby matching the second medical image data with the third medical image data. The processor 310 may generate, from the second medical image data, a second medical image on which the tissue extraction position is marked. The processor 310 may generate, from the third medical image data, a third medical image on which the previous tissue extraction position is marked and that is with respect to a cross-section of the object corresponding to the second medical image.

Figure 4A:
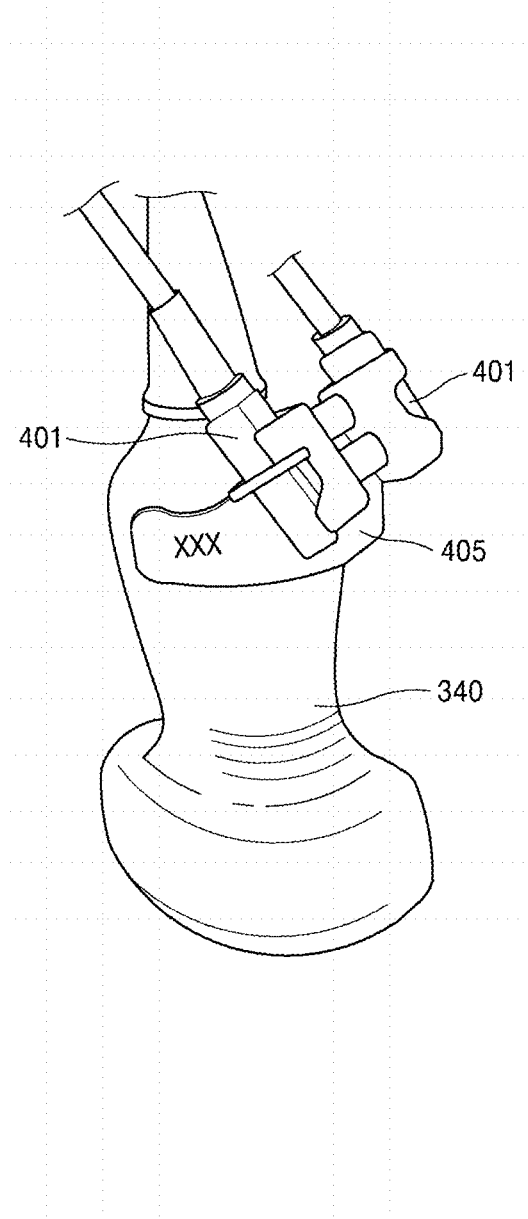
FIGS. 4A, 4B, and 4C illustrate examples of a position sensor attached to the probe, according to an exemplary embodiment.
Figure 4B:
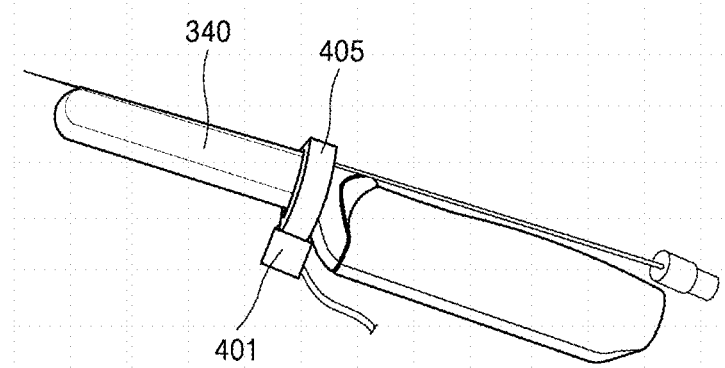
Figure 4C:
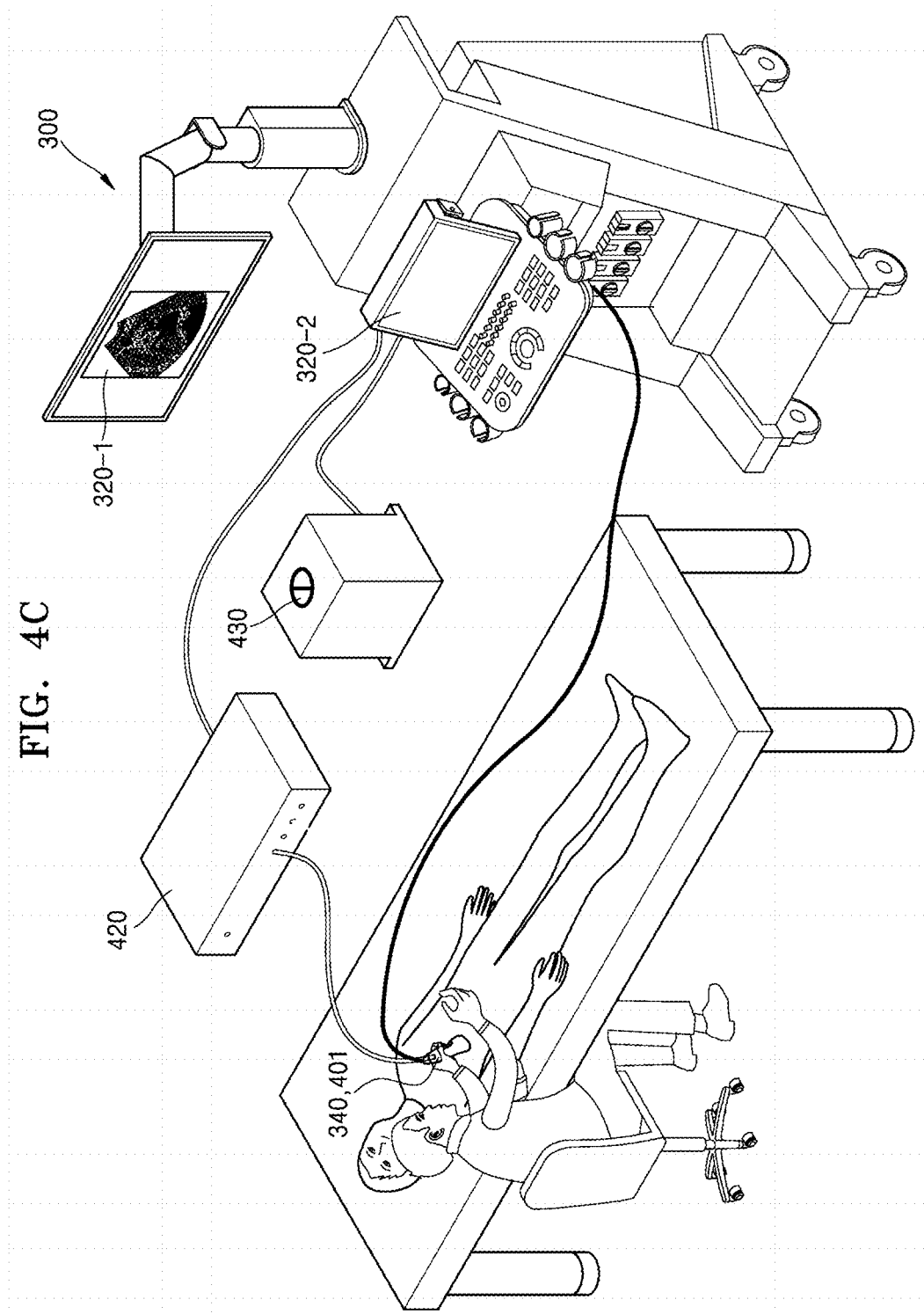

FIGS. 4A, 4B, and 4C illustrate examples of a position sensor 401 attached to the probe 340, according to exemplary embodiments.

As illustrated in FIG. 4A, the position sensor 401 may be fixed on an external surface of the probe 340 by a bracket 405. Referring to the example of FIG. 4A, two position sensors 401 are fixed on the probe 340 used to obtain an abdomen ultrasound image, but the present disclosure is not limited thereto.

FIG. 4B illustrates the example of one position sensor 401 that is fixed on the probe 340 by the bracket 405, the probe 340 being used to obtain an anus ultrasound image or a vagina ultrasound image. Referring to the examples of FIGS. 4A and 4B, the position sensor 401 is attached to the external surface of the probe 340, but according to another exemplary embodiment, a position sensor may be attached to a needle that performs a biopsy.

As illustrated in FIG. 4C, the position sensor 401 may detect an electromagnetic wave emitted by a field generator 430, and may transmit a detected signal to a signal input device 420. The position sensor 401 may detect a relative position of the position sensor 401 in an electromagnetic field generated by the field generator 430.

The medical image display apparatus 300 may obtain information about at least one of the probe 340 and a needle, based on a signal received from the signal input device 420. The medical image display apparatus 300 may determine a tissue extraction position in medial image data, based on the obtained information, and may display a medical image on which the tissue extraction position is marked on at least one of a first display 320-1 and a second display 320-2.

Hereinafter, a particular operating method of the medical image display apparatus 300 will be described. In exemplary embodiments, operations of the method to be described below may be performed by configurations of the medical image display apparatus 300 which are described above with reference to FIGS. 3A and 3B.

Figure 5A:
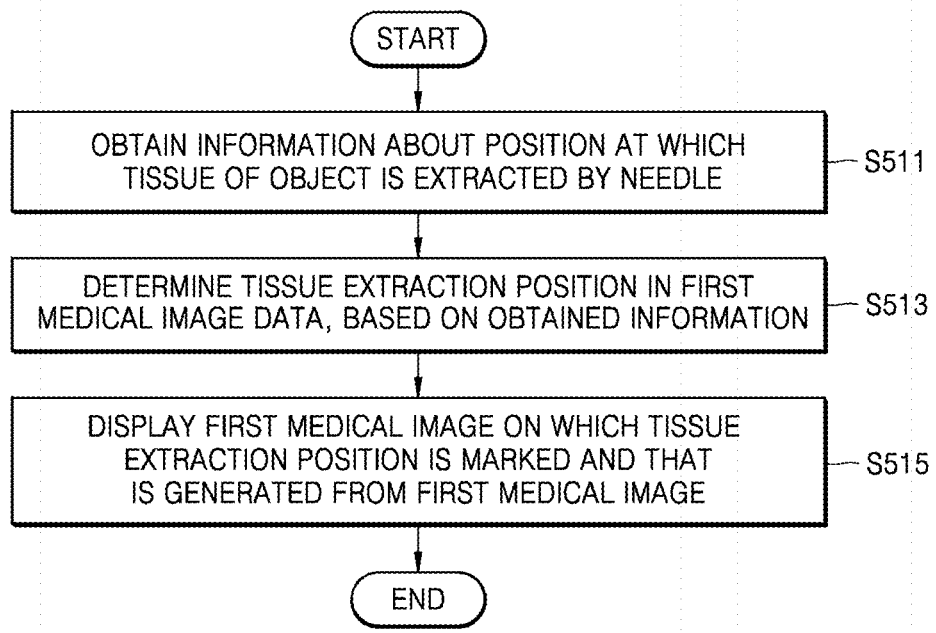
FIGS. 5A and 5B are flowcharts of a method of displaying a medical image, the method being performed by the medical image display apparatus, according to an exemplary embodiment.

FIG. 5A is a flowchart of a method of displaying a medical image, the method being performed by the medical image display apparatus 300, according to an exemplary embodiment. The medical image display apparatus 300 according to the present exemplary embodiment may display a medical image generated from medical image data obtained from an object by an ultrasound probe.

According to the present exemplary embodiment, in operation S511, the medical image display apparatus 300 may obtain information about a position at which tissue of the object is extracted by a needle, based on a signal received from a sensor attached to at least one of a probe and the needle. The medical image display apparatus 300 may obtain information about a position of the needle, based on the signal received from the sensor attached to at least one of the probe and the needle.

In operation S513, the medical image display apparatus 300 may determine a tissue extraction position in first medical image data, based on the information obtained in operation S511. For example, the first medical image data may include ultrasound image data. The medical image display apparatus 300 may match the first medical image data with the position of the needle, thereby determining, as the tissue extraction position, a point corresponding to the position of the needle when the needle extracts the tissue from the object.

In operation S515, the medical image display apparatus 300 may display a first medical image on which the tissue extraction position is marked and that is generated from the first medical image data. The medical image display apparatus 300 may mark the tissue extraction position on the first medical image by using at least one of a color, a figure, shading, and a sign.

Figure 10:
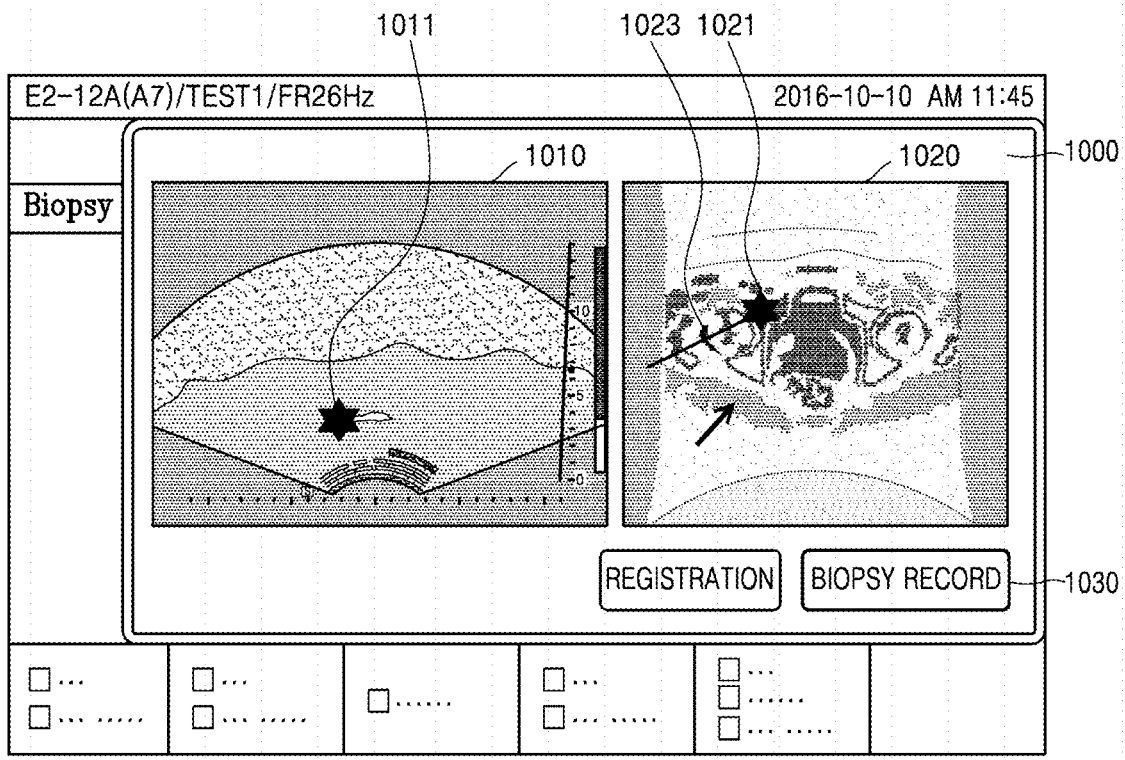
FIG. 10 illustrates an example in which the medical image display apparatus displays a screen image of a medical image on which a tissue extraction position is marked, according to an exemplary embodiment.

FIG. 10 illustrates an example in which the medical image display apparatus 300 displays a screen image 1000 of a medical image on which a tissue extraction position is marked, according to an exemplary embodiment. The medical image display apparatus 300 may display a first medical image 1010 on which a tissue extraction position 1011 is marked. The first medical image 1010 may be a real-time ultrasound image or a freeze-ultrasound image.

As illustrated in FIG. 10, the medical image display apparatus 300 may display not only an ultrasound image but may also display a medical image obtained by using at least one of various methods. For example, when a tissue extraction position is marked on the ultrasound image, the medical image display apparatus 300 may mark the tissue extraction position on another medical image related to the ultrasound image.

For example, while a biopsy is performed, the medical image display apparatus 300 may provide not only a real-time ultrasound image of an object but may also provide a CT image of a same part of the object, thereby providing information about an exact inner part of a body. When the tissue extraction position is marked on the ultrasound image, the medical image display apparatus 300 may also mark the tissue extraction position on the CT image provided with the ultrasound image.

Figure 5B:
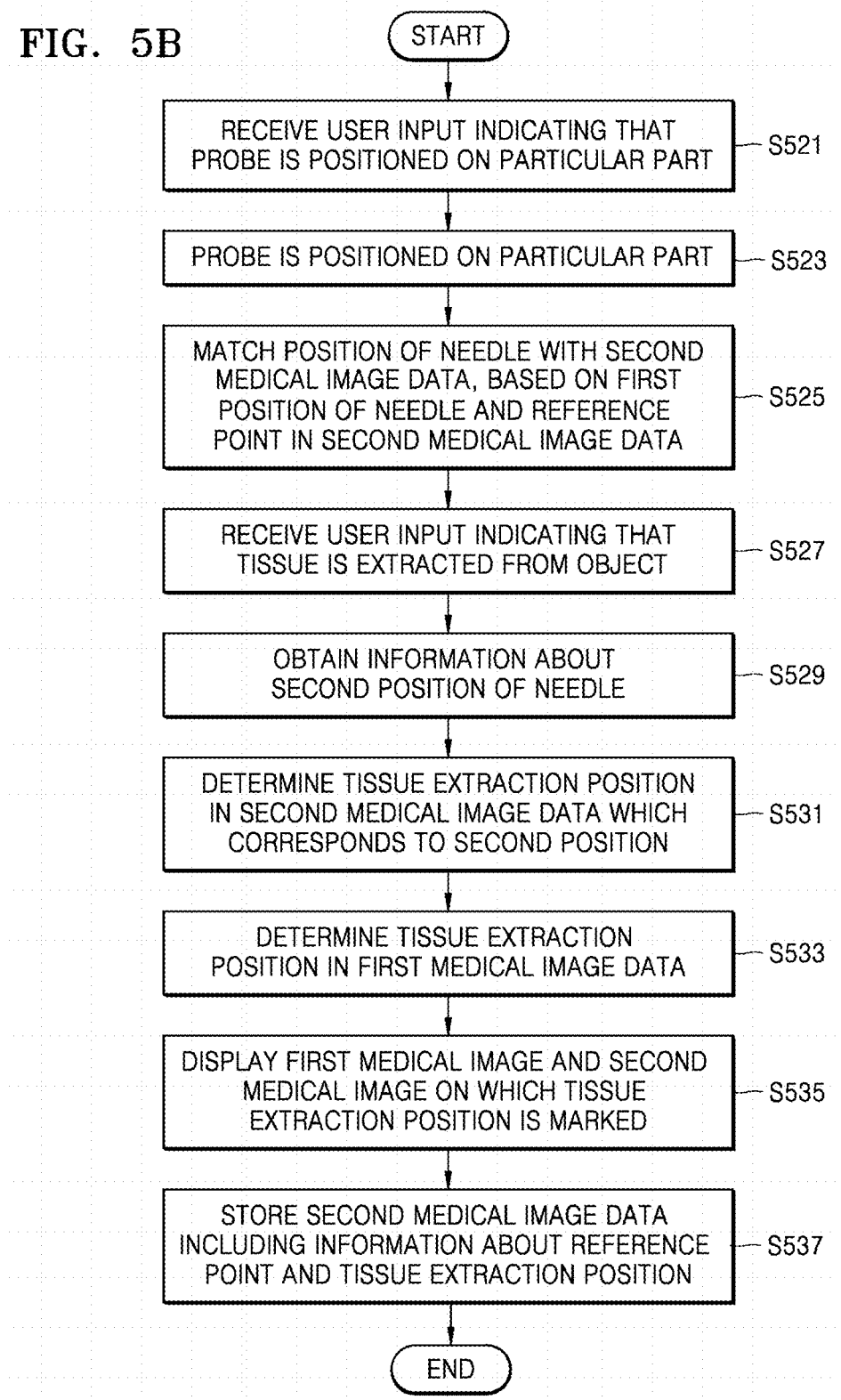

FIG. 5B is a flowchart of a method of displaying a medical image, the method being performed by a medical image display apparatus, according to an exemplary embodiment. Operation S511 of FIG. 5A may correspond to operations S521 through S529 of FIG. 5B, operation S513 of FIG. 5A may correspond to S533 of FIG. 5B, and operation S515 of FIG. 5A may correspond to operation S535 of FIG. 5B. For operations of FIG. 5A and operations of FIG. 5B which respectively correspond to each other, descriptions thereof may be applied to both of them. Thus, redundant descriptions thereof are omitted here.

According to the present exemplary embodiment, in operation S521, the medical image display apparatus 300 may receive a user input indicating that an ultrasound probe is positioned on a particular part.

The medical image display apparatus 300 may display a real-time ultrasound image generated from first medical image data that is obtained from an object using the ultrasound probe. When a user views the real-time ultrasound image displayed by the medical image display apparatus 300, the user may determine that the ultrasound probe is positioned on the particular part of the object. When the user determines that the ultrasound probe is positioned on the particular part, the user may input the user input to the medical image display apparatus 300.

Figure 7:
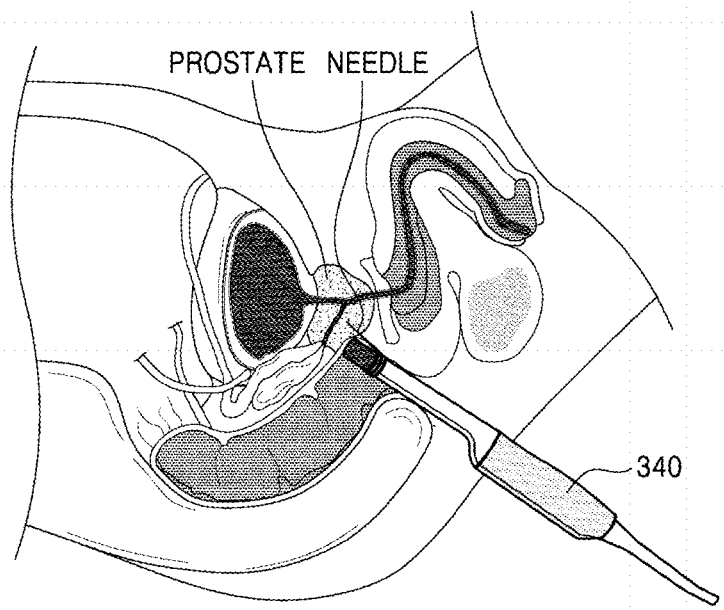
FIG. 7 is a diagram for describing a method of obtaining information about a first position of the needle, the method being performed by the medical image display apparatus, according to an exemplary embodiment.

For example, as illustrated in FIG. 7, in order to perform a prostate biopsy, the user may position the probe 340 to which an needle is attached on an anus. When the user views a real-time ultrasound image generated based on ultrasound data obtained by the probe 340, the user may determine that the probe 340 is positioned on a particular part. The particular part that is a reference part at which a position of a needle and medical image data are matched may be a part that is predetermined before a biopsy is performed. A tissue or an organ that varies less over time in the object may be predetermined as the particular part for the match.

In operation S523, the medical image display apparatus 300 may obtain information about a first position of the needle.

The medical image display apparatus 300 may obtain information about a position of the needle, based on a signal received from a sensor attached to at least one of the probe and the needle. The medical image display apparatus 300 may obtain a position of the sensor attached to at least one of the probe and the needle, as the information about the position of the needle.

Before tissue is extracted from the object by the needle, the medical image display apparatus 300 may obtain information about the first position of the needle, as a reference position with respect to a change in a position of the needle. When the user input is received, the medical image display apparatus 300 may obtain, as the information about the first position, information about a position of the needle at a point of time when the user input is received. The medical image display apparatus 300 may obtain, as the information about the first position, the information about the position of the needle located on the particular part of the object.

In operation S525, the medical image display apparatus 300 may match the position of the needle with the medical image data.

The medical image display apparatus 300 may obtain second medical image data obtained by using an image obtaining method different from that of the first medical image data. For example, the second medical image data may include at least one of MR image data, CT image data, and model image data obtained by modeling the object.

The medical image display apparatus 300 may match the position of the needle with the second medical image data. The medical image display apparatus 300 may match the first position of the needle with a reference point in the second medical image data, thereby matching the position of the needle with the second medical image data.

For example, the reference point in the second medical image data may be a position corresponding to the first position of the needle. The reference point in the second medical image data may be a point corresponding to the particular part in the object. The reference point in the second medical image data may be pre-stored or may be determined based on a user input. For example, when the prostate biopsy is performed, the medical image display apparatus 300 may match the first position of the needle, which is obtained when the ultrasound probe is positioned in an anus of a patient, with a reference point in the first medical image data which corresponds the anus, thereby matching the position of the needle with the second medical image data.

The medical image display apparatus 300 may match the position of the needle with the second medical image data, thereby determining a position in the second medical image data which corresponds to a current position of the needle.

Figure 8:
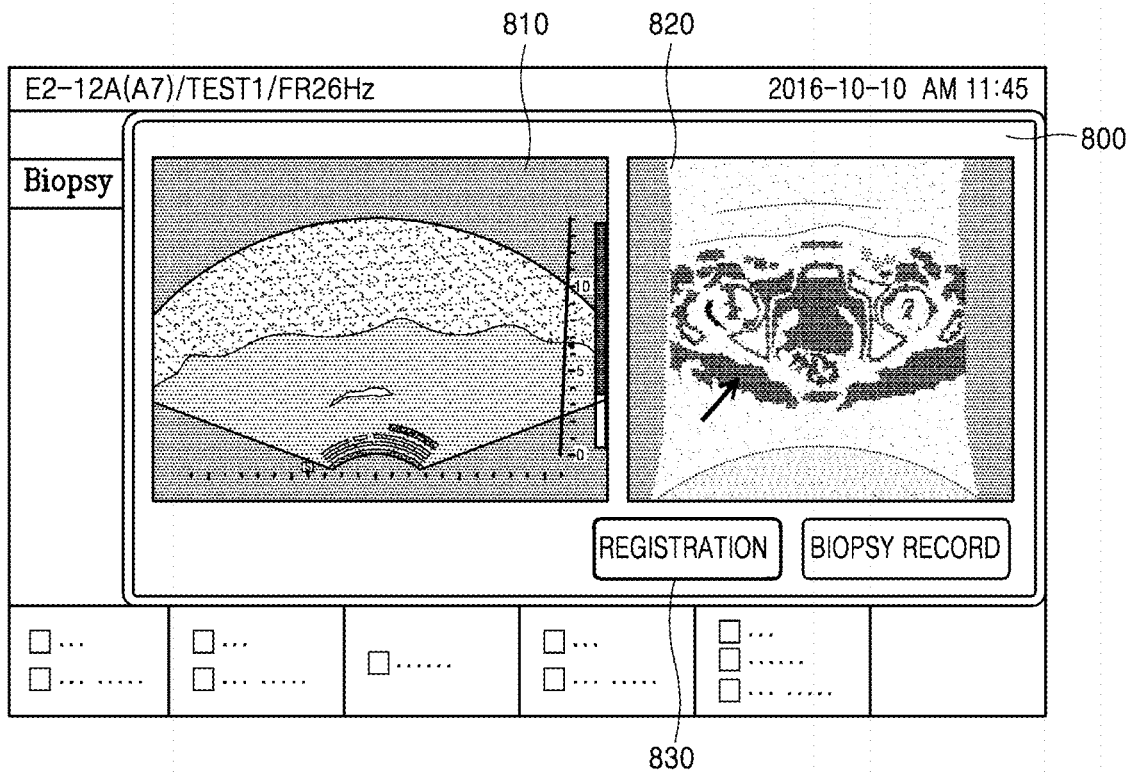
FIG. 8 illustrates an example of a screen image for receiving a user input via the medical image display apparatus, in order to match a position of a needle with medical image data, according to an exemplary embodiment.

FIG. 8 illustrates an example of a screen image 800 for receiving a user input in order to match a position of a needle with medical image data, according to an exemplary embodiment.

For example, the medical image display apparatus 300 may obtain ultrasound image data obtained by a probe to which a needle is attached, and may display a real-time ultrasound image 810 generated from the ultrasound image data. According to the present exemplary embodiment, in order to increase an accuracy of a biopsy, the medical image display apparatus 300 may display not only the real-time ultrasound image 810 but may also display a medical image 820 such as an MR image, a CT image, or a model image which is obtained by using a different image obtaining method.

When a user determines that the probe is positioned on the particular part by referring to the real-time ultrasound image 810, the medical image display apparatus 300 may input a user input for controlling the medical image display apparatus 300 to match the position of the needle with the ultrasound image data. When a user input of selecting a button 830 is received, the medical image display apparatus 300 may obtain, as information about a first position, information about a position of the needle at that point of time, and may match the position of the needle with the ultrasound image data.

According to the present exemplary embodiment, in operation S527, the medical image display apparatus 300 may receive a user input indicating that tissue is extracted from an object. The user may input the user input to the medical image display apparatus 300 before the tissue is extracted from the object by using the needle, when the tissues is extracted, or after the tissue is extracted.

In operation S529, the medical image display apparatus 300 may obtain information about a second position of the needle.

The information about the second position of the needle may include information about a position at which tissue of the object is extracted by the needle. When the user input is received, the medical image display apparatus 300 may obtain, as the information about the second position, information about a position of the needle at a point of time when the user input is received. The medical image display apparatus 300 may obtain, as the information about the second position, coordinate information corresponding to the second position in a coordinate system including the first position as a starting point.

Figure 9:
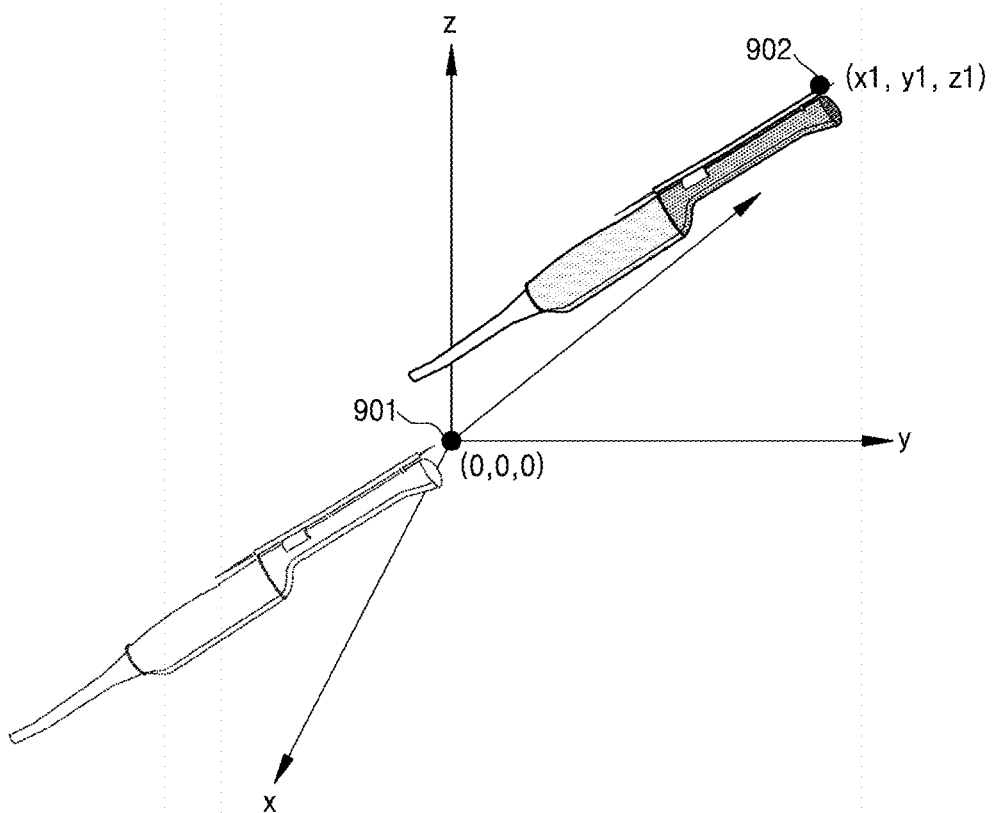
FIG. 9 is a diagram for describing information about a stored tissue extraction position, according to an exemplary embodiment.

As illustrated in FIG. 9, the medical image display apparatus 300 may obtain coordinate information, for example coordinates x1, y1, z1, corresponding to a changed position 902 in a coordinate system including a first position 901 of a needle as a starting point.

For example, information about a position of the needle may be obtained by a position sensor included in a probe to which the needle is attached. When the medical image display apparatus 300 receives a user input indicating that tissue is extracted from the object, the medical image display apparatus 300 may obtain information about a position of the probe to which the needle is attached. The medical image display apparatus 300 may determine the information about the second position, based on at least one of a distance and a direction in which the needle has moved with respect to the probe in order to extract the tissue. The distance and the direction in which the needle has moved with respect to the probe in order to extract the tissue may be predetermined values. Thus, the medical image display apparatus 300 may compensate for the distance by which the needle has moved from the position of the probe, thereby obtaining the information about the position at which the tissue is extracted by the needle.

In operation S531, the medical image display apparatus 300 may determine or locate a tissue extraction position in the second medical image data which corresponds to the second position.

The medical image display apparatus 300 may determine the tissue extraction position in the second medical image data, based on a result of matching the position of the needle with the second medical image data. The medical image display apparatus 300 may match the position of the needle with the second medical image data, thereby obtaining transformation information for transforming the position of the needle to a predetermined point in the second medical image data.

The medical image display apparatus 300 may determine the tissue extraction position with respect to a reference point, based on the coordinate information corresponding to the second position in the coordinate system including the first position as a starting point. The medical image display apparatus 300 may determine the tissue extraction position in the second medical image data which corresponds to the second position, based on the coordinate information and the transformation information.

In operation S533, the medical image display apparatus 300 may determine or locate a tissue extraction position in the first medical image data.

For example, the medical image display apparatus 300 may determine the tissue extraction position in the first medical image data, based on the information about the position at which the tissue is extracted by the needle. The first medical image data may include ultrasound image data.

The medical image display apparatus 300 may match the first medical image data with the position of the needle, thereby determining, as the tissue extraction position, a point corresponding to the position of the needle at a point of time when the tissue is extracted from the object.

As another example, the medical image display apparatus 300 may determine the tissue extraction position by analyzing the medical image generated from the first medical image data. For example, the medical image display apparatus 300 may determine a trajectory of movement of the needle by comparing a reference medical image obtained from the object before extraction of the tissue with medical images obtained from the object in order to track the movement of the needle while the tissue is being extracted. The medical image display apparatus 300 may determine the tissue extraction position based on the trajectory of the movement of the needle.

In operation S535, the medical image display apparatus 300 may display the first medical image and the second medical image on which the tissue extraction position is marked. The medical image display apparatus 300 may display the tissue extraction position on the medical images by using at least one of a color, a figure, shading, and a sign.

The tissue extraction position marked on the medical image may be amended based on a user input. When the user determines that the marked tissue extraction position is different from an actual tissue extraction position, the marked tissue extraction position being automatically determined by the medical image display apparatus 300, the user may input the user input of amending the determined or marked tissue extraction position to the medical image display apparatus 300. The medical image display apparatus 300 may amend the tissue extraction position in the medical image data, based on the received user input, and may mark an amended tissue extraction position on the medical image.

In operation S537, the medical image display apparatus 300 may store the medical image data including information about the reference point and the tissue extraction position. In addition, the medical image display apparatus 300 may further store information about the second position of the needle at which the tissue is extracted from the object. The medical image display apparatus 300 may store, as the information about the second position of the needle, the coordinate information corresponding to the second position of the needle in the coordinate system including the first position of the needle as a starting point.

The medical image display apparatus 300 according to the present exemplary embodiment may store the medical image data including the information about the tissue extraction position with respect to the reference point, so that the user may intuitively compare positions for biopsies performed at different times.

The medical image display apparatus 300 may store third medical image data including information about a reference point and a previous tissue extraction position, in relation to a biopsy that was previously performed on the object. The medical image display apparatus 300 may obtain the stored third medical image data. The medical image display apparatus 300 may match the reference point of the second medical image data with the reference point of the third medical image data, thereby matching the second medical image data with the third medical image data. The medical image display apparatus 300 may rapidly and accurately match the second medical image data with the third medical image data by matching preset reference points. The medical image display apparatus 300 may generate the second medical image on which the tissue extraction position is marked from the second medical image data. The medical image display apparatus 300 may generate a third medical image on which the previous tissue extraction position is marked from the third medical image data. The medical image display apparatus 300 may generate the third medical image with respect to a cross-section of the object corresponding to the second medical image. For example, the medical image display apparatus 300 may generate the third medical image with respect to a same cross-section as the cross-section of the object which is displayed on the second medical image. The medical image display apparatus 300 may display the second medical image and the third medical image. For example, the medical image display apparatus 300 may overlap and display the second medical image and the third medical image.

Accordingly, the medical image display apparatus 300 displays the tissue extraction positions respectively on the medical images of the same cross-section of the object, so that the user may intuitively compare positions for biopsies performed at different times.

As described above with reference to FIGS. 5A and 5B, the medical image display apparatus 300 may determine the tissue extraction position in the first medical image data obtained from the object by the probe, and may automatically mark the tissue extraction position on the first medical image. However, the medical image on which the medical image display apparatus 300 automatically records the tissue extraction position is not limited to the ultrasound image generate from the medical image data obtained from the object by the probe. The medical image display apparatus 300 may mark a tissue extraction position on a medical image obtained by using at least one of various methods.

Figure 6A:
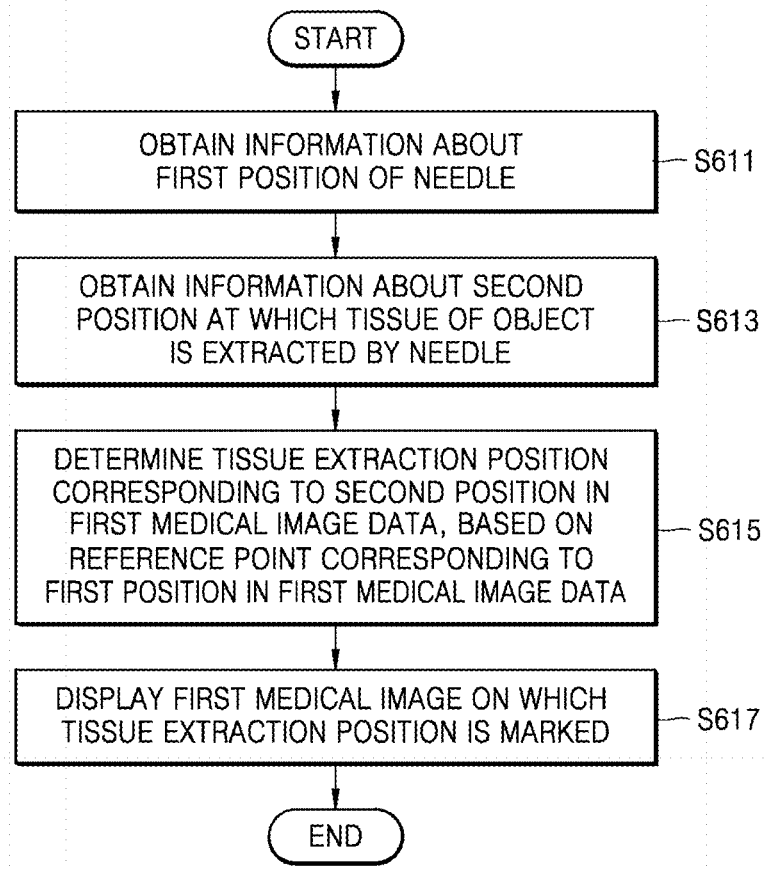
FIGS. 6A and 6B are flowcharts of a method of displaying a medical image, the method being performed by the medical image display apparatus, according to another exemplary embodiment.

FIG. 6A is a flowchart of a method of displaying a medical image, the method being performed by a medical image display apparatus, according to another exemplary embodiment.

According to the present exemplary embodiment, in operation S611, the medical image display apparatus 300 may obtain information about a first position of a needle. Before tissue is extracted from an object by using the needle, the medical image display apparatus 300 may obtain the information about a first position of the needle, as reference information.

Information about a position of the needle may be obtained by a position sensor included at least one of the needle and a probe to which the needle is attached. The needle for a biopsy may be attached to the probe used to obtain ultrasound image data. Thus, the medical image display apparatus 300 may determine that the needle corresponds to a position of the probe, and may obtain information about the position of the probe as the information about a position of the needle.

The medical image display apparatus 300 may obtain the ultrasound image data obtained by the probe to which the needle is attached, and may display a real-time ultrasound image generated from the ultrasound image data. When a user of the medical image display apparatus 300 checks the real-time ultrasound image, the user may move the probe to which the needle is attached in order to position the probe on a reference part of the object. When the probe to which the needle is attached is positioned on the reference part of the object while the user checks the real-time ultrasound image, the user of the medical image display apparatus 300 may input a first input to the medical image display apparatus 300. When the first input is received, the medical image display apparatus 300 may obtain, as the information about the first position, information about a position of the needle at a point of time corresponding to the reception.

The medical image display apparatus 300 may obtain first medical image data. For example, the first medical image data may include at least one of MR image data, CT image data, and model image data obtained by modeling the object.

The medical image display apparatus 300 may match the position of the needle with the first medical image data. The medical image display apparatus 300 may match the first position of the needle with a reference point in the first medical image data, thereby matching the position of the needle with the first medical image data. The reference point in the first medical image data may be determined based on pre-stored information or a user input. The reference point may be a point corresponding to a particular part of the object. For example, in a prostate biopsy, the reference point may be an anus.

In operation S613, the medical image display apparatus 300 may obtain information about a second position at which tissue of the object is extracted by the needle.

The medical image display apparatus 300 may detect a change in a position of the needle with respect to the first position. For example, the medical image display apparatus 300 may obtain, as information about a second position, coordinate information corresponding to the second position in a coordinate system including the first position as a starting point.

When the user of the medical image display apparatus 300 checks the real-time ultrasound image, the user may move the probe in order to make the needle attached to the probe positioned within a part of interest or near the part of interest. When the needle attached to the probe is positioned in the part of interest while the user of the medical image display apparatus 300 checks the real-time ultrasound image, the user may input a second input to the medical image display apparatus 300. When the second input is received, the medical image display apparatus 300 may obtain, as the information about the second position, information about a position of the needle at a point of time corresponding to the reception. The medical image display apparatus 300 may obtain, as the information about the second position, the information about the position of the needle before the tissue is extracted from the part of interest with respect to the object by using the needle, when the tissue is extracted, or right after the tissue is extracted.

The needle attached to the probe may move in a predetermined direction with respect to the probe in order to extract the tissue and then may return to its original position. When a user input indicating that the needle is positioned in the part of interest is received, the medical image display apparatus 300 may obtain information about a position of the probe to which the needle is attached. The medical image display apparatus 300 may determine the information about the second position, based on a distance and a direction in which the needle has moved with respect to the probe in order to extract the tissue, and the position of the probe.

In operation S615, the medical image display apparatus 300 may determine a tissue extraction position in the first medical image data. The medical image display apparatus 300 may determine the tissue extraction position corresponding to the second position in the first medical image data. The medical image display apparatus 300 may determine the tissue extraction position corresponding to the second position in the first medical image data, based on the reference point in the first medical image data of the object, the reference point corresponding to the first position.

The medical image display apparatus 300 may determine the tissue extraction position to correspond to the second position of the needle in the first medical image data, based on a result of matching the position of the needle with the first medical image data. The medical image display apparatus 300 may determine a point of the tissue extraction position with respect to the reference point in the first medical image data, based on a change in a position of the needle that has moved from the first position to the second position. For example, the medical image display apparatus 300 may determine the tissue extraction position with respect to the reference point, based on the coordinate information corresponding to the second position in the coordinate system including the first position as a starting point.

In operation S617, the medical image display apparatus 300 may generate, from the first medical image data, and display a first medical image on which the tissue extraction position is marked. The medical image display apparatus 300 may display not only the first medical image but may also display an ultrasound image on which the tissue extraction position is marked.

The medical image display apparatus 300 may automatically mark the tissue extraction position, thereby reducing a time period that is additionally required to manually mark the tissue extraction position. In addition, the medical image display apparatus 300 has merits because an operation assistant to manually mark the tissue extraction position is not required.

The medical image display apparatus 300 may store medical image data including information about the reference point and the tissue extraction position. Thus, the medical image display apparatus 300 may match the first medical image data with the second medical image data based on the reference point, in relation to the first medical image data and the second medical image data related to biopsies that were performed at different times.

The medical image display apparatus 300 may generate medical images of a same cross-section of the object from the matched second medical image data and second medical image data. The medical image display apparatus 300 may mark the tissue extraction positions on the generated medical images. Thus, the medical image display apparatus 300 may display, in an intuitive manner for a user, a change in the positions from which tissue is extracted when the biopsies are performed at different times.

Figure 6B:
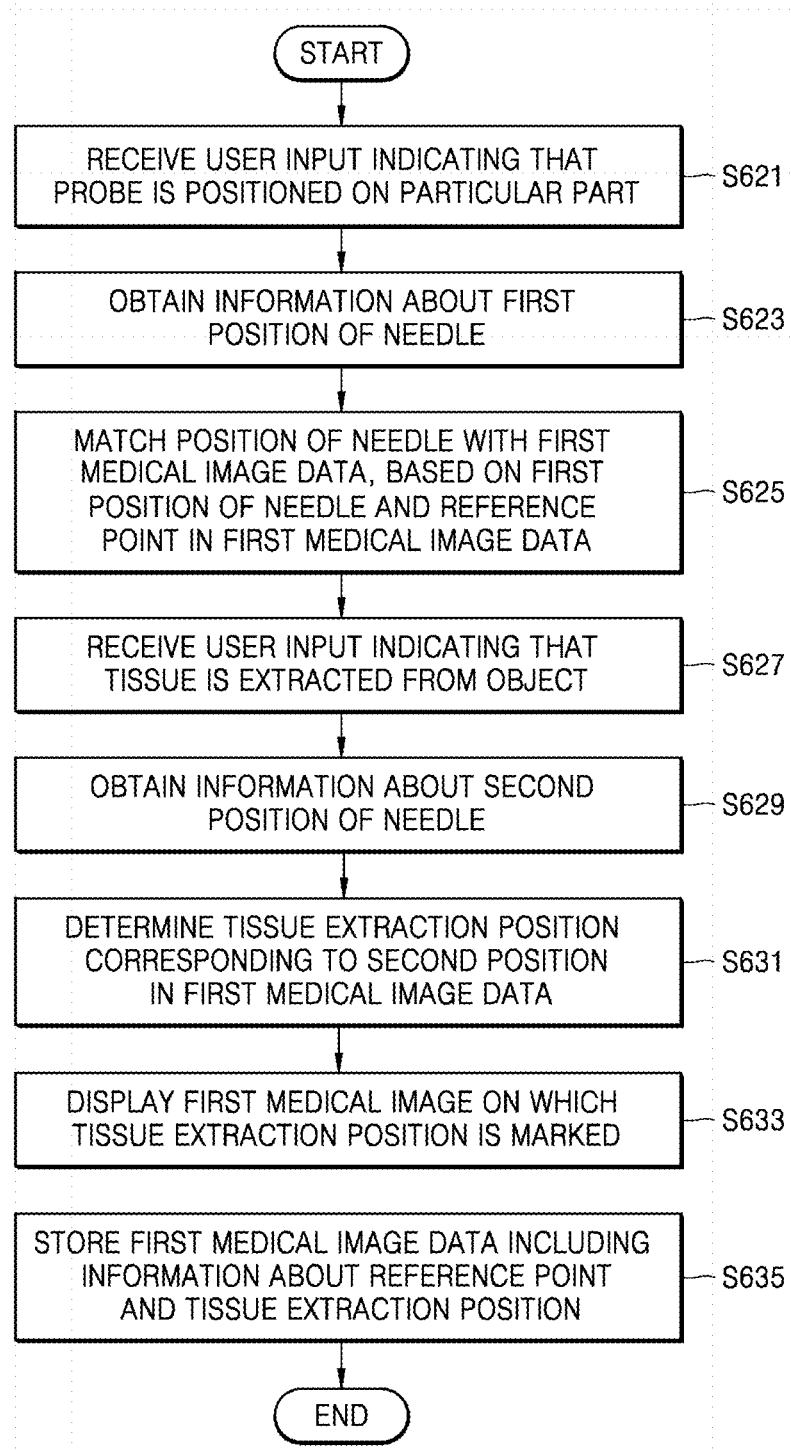

FIG. 6B is a flowchart of a method of displaying a medical image, the method being performed by a medical image display apparatus, according to another exemplary embodiment. Operation S611, S613, S615, and S617 of FIG. 6A may respectively correspond to operations S623, S629, S631, and S633 of FIG. 6B, respectively. For operations of FIG. 6A and operations of FIG. 6B which respectively correspond to each other, descriptions thereof may be applied to both of them. Thus, redundant descriptions thereof are omitted here.

According to the present exemplary embodiment, in operation S621, the medical image display apparatus 300 may receive a user input indicating that a probe is positioned on a particular part of an object.

For example, when a prostate biopsy is performed, when an ultrasound probe is positioned in an anus of a patient, a user may input the user input to the medical image display apparatus 300.

In operation S623, the medical image display apparatus 300 may obtain information about a first position of a needle. Before tissue is extracted from the object by using the needle, the medical image display apparatus 300 may obtain the information about the first position of the needle, as reference information. When the user input is received in operation S621, the medical image display apparatus 300 may obtain, as the information about the first position, information about a position of the needle at a point of time corresponding to the reception.

In operation S625, the medical image display apparatus 300 may match a position of the needle with first medical image data.

FIG. 8 illustrates the example of the screen image 800 for receiving the user input in order to match the position of the needle with medical image data, according to an exemplary embodiment.

As illustrated in FIG. 8, the medical image display apparatus 300 may obtain the ultrasound image data obtained by the probe to which the needle is attached, and may display the real-time ultrasound image 810 generated from the ultrasound image data.

According to the present exemplary embodiment, in order to increase an accuracy of the biopsy, the medical image display apparatus 300 may display not only the real-time ultrasound image 810 but may also display the medical image 820 such as an MR image, a CT image, or a model image which is obtained by using a different image obtaining method. The medical image 820 may be an image obtained from first medical image data. Because the screen image 800 corresponds to an image before a position of the needle or the probe and the first medical image data are matched, the medical image 820 that is generated from the first medical image data and is of a random cross-section of the object may be displayed thereon.

The medical image 820 may be an image on which a reference point determined based on pre-stored information or a user input is marked. The reference point in the first medical image data may be a point corresponding to a particular part of the object. For example, in a prostate biopsy, the reference point may be an anus.

The medical image display apparatus 300 may mark the reference point on the medical image 820, based on pre-stored information in association with a part to which a biopsy is to be performed.

In exemplary embodiments, the medical image display apparatus 300 may display a point corresponding to a user input, as the reference point, based on the user input with respect to the medical image 820. For example, the user may set, as the reference point, a point at which the needle attached to the probe is expected to be positioned, based on a real-time ultrasound image obtained by the probe.

When the user determines that the probe is positioned on the particular part by referring to the real-time ultrasound image 810, the user may input a user input for controlling the medical image display apparatus 300 to match a position of the needle with the first medical image data. When a user input of selecting the button 830 is received, the medical image display apparatus 300 may obtain, as information about a first position, information about a position of the needle at a point of time corresponding to the reception, and may match the position of the needle with the first medical image data. The medical image display apparatus 300 may automatically match the position of the needle with the first medical image data, and may compensate for a result of the match based on a user input.

According to the present exemplary embodiment, the medical image display apparatus 300 may match the first position of the needle with the reference point in the first medical image data, thereby matching the position of the needle with the first medical image data. The medical image display apparatus 300 may calculate the point in the first medical image data which corresponds to the position of the needle that is moved by the user, based on the result of the match.

As illustrated in FIG. 9, the medical image display apparatus 300 may obtain the coordinate information, for example coordinates x1, y1, z1 corresponding to the changed position 902 in the coordinate system including the first position 901 of the needle as a starting point.

According to the present exemplary embodiment, in operation S627, the medical image display apparatus 300 may receive a user input indicating that tissue is extracted from the object.

When the needle attached to the probe is positioned on a part of interest while the user of the medical image display apparatus 300 checks the real-time ultrasound image, the user may extract the tissue by manipulating the needle. The user may input the user input to the medical image display apparatus 300 before the tissue is extracted from the object, when the tissue is extracted, or after the tissue is extracted.

In operation S629, the medical image display apparatus 300 may obtain information about a second position at which the tissue of the object is extracted by the needle. When the user input is received in operation S627, the medical image display apparatus 300 may obtain, as the information about the second position, information about a position of the needle at a point of time corresponding to the reception.

In operation S631, the medical image display apparatus 300 may determine a tissue extraction position corresponding to the second position in the first medical image data.

The medical image display apparatus 300 may determine the tissue extraction position corresponding to the second position of the needle in the first medical image data, based on a result of matching the position of the needle with the first medical image data.

In operation S633, the medical image display apparatus 300 may generate, from the first medical image data, and display the first medical image on which the tissue extraction position is marked.

FIG. 10 illustrates the example in which the medical image display apparatus 300 displays the screen image 1000 of the medical image on which the tissue extraction position is marked, according to an exemplary embodiment.

Because tissue has been extracted from an object, when a user input of requesting to record the tissue extraction position is received, the medical image display apparatus 300 may obtain information about a second position of a needle. The medical image display apparatus 300 may determine the tissue extraction position corresponding to the second position in first medical image data, and may display a first medical image on which the determined tissue extraction position is marked. For example, the user input of requesting to record the tissue extraction position may include a user input of selecting a button 1030 on the screen image 1000.

The medical image display apparatus 300 may display a second medical image 1020 on which a tissue extraction position 1021 is marked. The medical image display apparatus 300 may further include an indicator 1023 indicating an insertion direction of the needle based on a direction in which the needle has moved to extract the tissue.

The medical image display apparatus 300 may display the first medical image 1010 generated from ultrasound image data obtained by a probe to which the needle is attached. The medical image display apparatus 300 may mark the tissue extraction position 1011 on the first medical image 1010. For example, the medical image display apparatus 300 may determine the tissue extraction position 1011 based on at least one of a distance and a direction in which the needle has moved with respect to the probe in order to extract the tissue, and may mark the tissue extraction position 1011 on the first medical image 1010. The first medical image 1010 may be an ultrasound image such as a real-time ultrasound image or a freeze-ultrasound image.

The medical image display apparatus 300 may amend an automatically-marked tissue extraction position, in response to a user input. The medical image display apparatus 300 may move a marker for displaying a tissue extraction position to an amended position and display the marker. The medical image display apparatus 300 may amend an automatically-determined tissue extraction position to a position amended based on the user input and may store the amended position.

Figure 11:
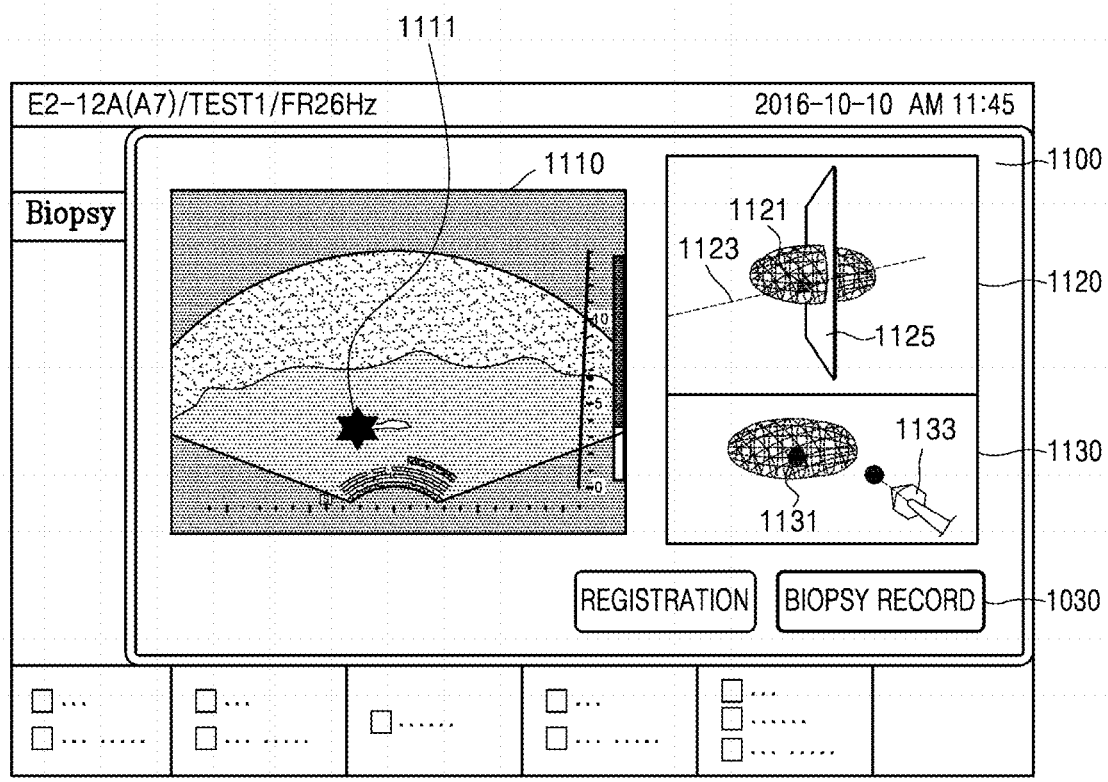
FIG. 11 illustrates an example of a screen image on which a tissue extraction position is marked, according to another exemplary embodiment.

FIG. 10 illustrates the example in which MR image data is used as the second medical image data. However, the present exemplary embodiment is not limited thereto. As illustrated in FIG. 11, the medical image display apparatus 300 may display a medical image on which a tissue extraction position is marked, by using model image data obtained by modeling an object.

FIG. 11 illustrates an example of a screen image 1100 on which a tissue extraction position is marked, according to another exemplary embodiment.

When a user input of selecting a button 1030 on the screen image 1100 is received, the medical image display apparatus 300 may display a first medical image 1120 on which a tissue extraction position 1121 is marked. The first medical image 1120 is a model image generated from model image data obtained by modeling tissue or an organ of an object. The medical image display apparatus 300 may further display an indicator 1123 indicating an insertion direction of a needle based on a direction in which the needle has moved to extract tissue. The medical image display apparatus 300 may further display an indicator 1125 indicating a predetermined cross-section of the object. The indicator 1125 may indicate a cross-section corresponding to an ultrasound image 1110, may indicate a cross-section including a position at which tissue is extracted, or may indicate a cross-section corresponding to the second medical image 1020 included in the screen image 1000 displayed before the screen image 1100 is displayed.

The medical image display apparatus 300 may further display a medical image 1130 generated by rendering the model image data to have a different viewpoint. The medical image display apparatus 300 may further display, on the medical image 1130, a tissue extraction position 1131 and an indicator 1133 indicating an insertion direction of the needle.

The medical image display apparatus 300 may display an ultrasound image 1110 generated from ultrasound image data obtained by a probe to which the needle is attached. The medical image display apparatus 300 may display a tissue extraction position 1111 on the ultrasound image 1110.

Referring back to FIG. 6B, in operation S635, the medical image display apparatus 300 may store the first medical image data including information about a reference point and a tissue extraction position.

The medical image display apparatus 300 may store medical image data including information about a reference point and a tissue extraction position with respect to the reference point, so that the medical image display apparatus

300 may display at a later time the tissue extraction position related to a previously-performed biopsy, in an intuitive manner for a user.

For example, the medical image display apparatus 300 may store second medical image data including information about a reference point and a previous tissue extraction position, in relation to the previously-performed biopsy. The medical image display apparatus 300 may generate and display medical images on which the tissue extraction positions are marked, by using the first medical image data and the second medical image data related to biopsies that were performed at different times. Thus, the medical image display apparatus 300 may display, in an intuitive manner for a user, a change in the tissue extraction positions with respect to the biopsies that were performed at different times.

Figure 12:
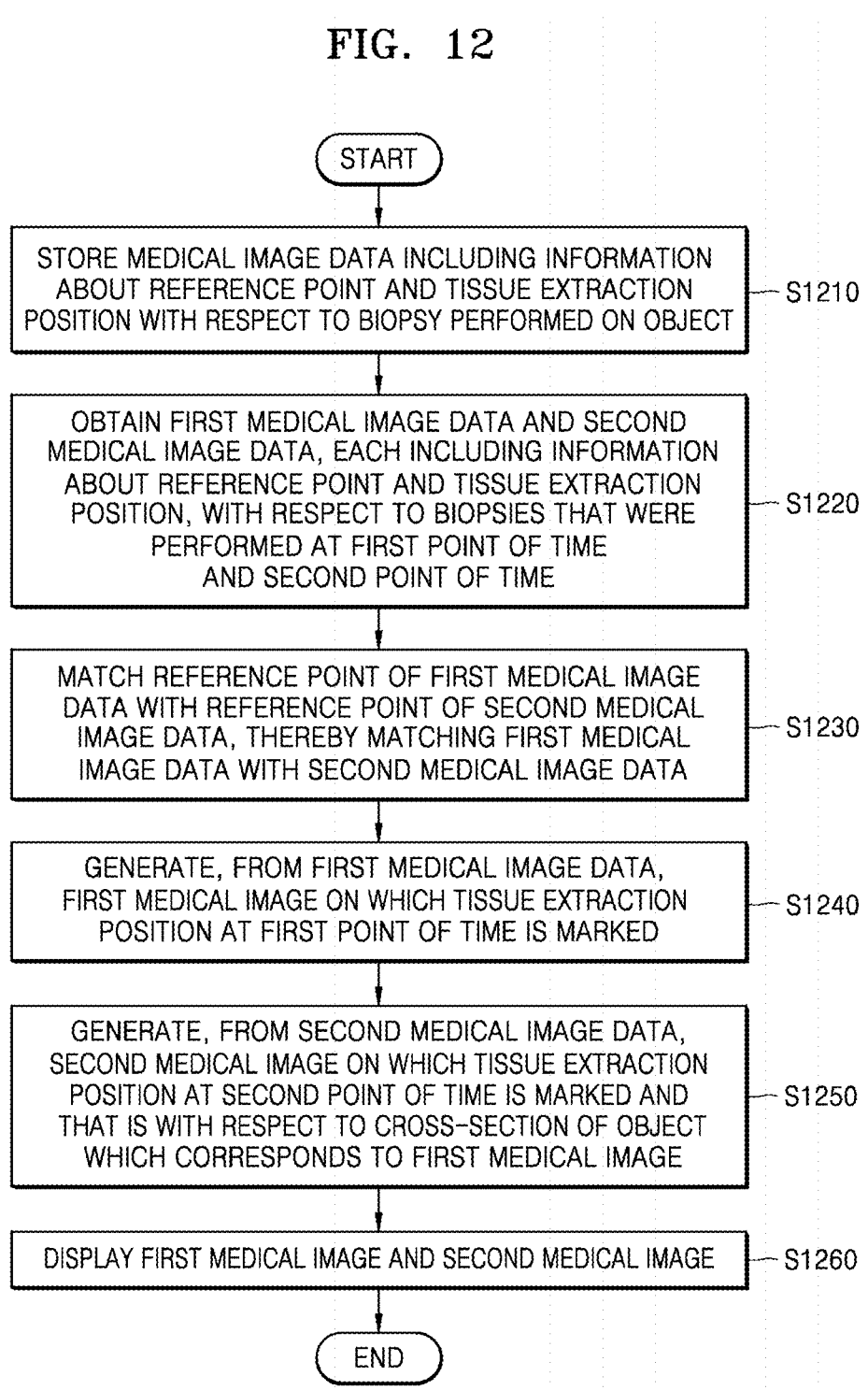
FIG. 12 is a flowchart of a method of displaying medical images on which tissue extraction positions with respect to different time zones are marked, the method being performed by the medical image display apparatus, according to an exemplary embodiment.

FIG. 12 is a flowchart of a method of displaying medical images on which tissue extraction positions with respect to different times are marked, the method being performed by the medical image display apparatus 300, according to an exemplary embodiment.

In operation S1210, the medical image display apparatus 300 may store medical image data including information about a reference point and a tissue extraction position with respect to a biopsy performed on an object. The method described above with reference to FIG. 5A, 5B, 6A, or 6B may be used as a method of determining a tissue extraction position in medical image data. The medical image display apparatus 300 may store a plurality of items of medical image data related to biopsies that were performed at different times.

In operation S1220, the medical image display apparatus 300 may obtain first medical image data and second medical image data, each including information about a reference point and a tissue extraction position, with respect to biopsies that were performed at a first point of time and a second point of time. The medical image display apparatus 300 may obtain medical image data from an embedded memory or an external server.

In operation S1230, the medical image display apparatus 300 may match the reference point of the first medical image data with the reference point of the second medical image data, thereby matching the first medical image data with the second medical image data. For example, each reference point may be a preset point that corresponds to a particular part in the object. Thus, the medical image display apparatus 300 may rapidly and accurately match the first medical image data with the second medical image data by matching the preset reference points.

In operation S1240, the medical image display apparatus 300 may generate, from the first medical image data, a first medical image on which the tissue extraction position at the first point of time is marked. The reference point may be further displayed on the first medical image.

In operation S1250, the medical image display apparatus 300 may generate, from the second medical image data, a second medical image on which the tissue extraction position at the second point of time is marked. The medical image display apparatus 300 may generate the second medical image of a cross-section of the object which corresponds to the first medical image. For example, the medical image display apparatus 300 may generate the second medical image showing a same cross-section as the cross-section of the object which is displayed on the first medical image. The reference point may be further displayed on the second medical image.

In operation S1260, the medical image display apparatus 300 may display the first medical image and the second medical image. For example, the medical image display apparatus 300 may display the second medical image in the vicinity of the first medical image, or may overlap and display the first medical image and the second medical image.

Figure 13:
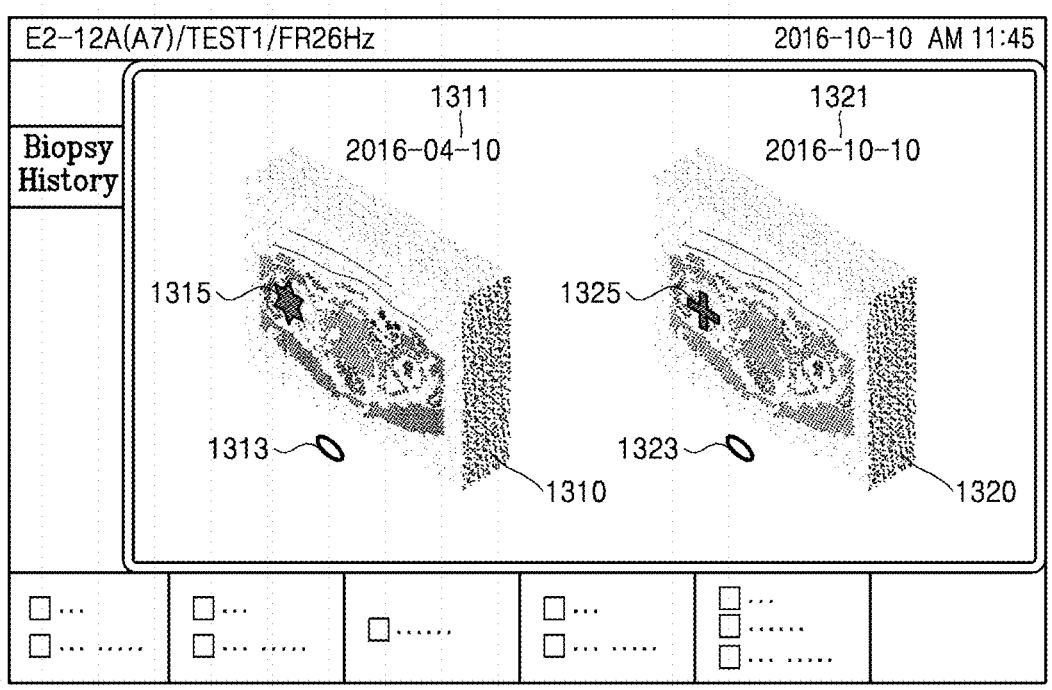
FIG. 13 illustrates an example of a screen image displaying medical images on which tissue extraction positions with respect to different time zones are marked, according to an exemplary embodiment.

FIG. 13 illustrates an example of a screen image displaying medical images on which tissue extraction positions from different times are marked, according to an exemplary embodiment.

The medical image display apparatus 300 may fetch medical image data related to biopsies that were performed at different times. For example, the medical image display apparatus 300 may fetch first medical image data and second medical image data related to the biopsies that were performed at different times. The medical image display apparatus 300 may match the first medical image data with the second medical image data, based on reference points stored together with medical image data.

According to the present exemplary embodiment, the medical image display apparatus 300 may generate and display medical images of a same cross-section of an object from respective first medical image data and second medical image data, based on a result of the match. The medical image display apparatus 300 may display, on the medical images, tissue extraction positions recorded as positions relative to the reference points, respectively.

When a user input for viewing a biopsy history is received, the medical image display apparatus 300 may display a first medical image 1320 on which a reference point 1323 and a tissue extraction position 1325 are marked. The medical image display apparatus 300 may display not only the first medical image 1320 but may also display information 1321 about a time at which a biopsy was performed.

The medical image display apparatus 300 may obtain second medical image data including information about a reference point and a previous tissue extraction position related to a biopsy that was previously performed. The medical image display apparatus 300 may display a second medical image 1310 on which a reference point 1313 and a tissue extraction position 1315 are marked. The medical image display apparatus 300 may display not only the second medical image 1310 but may also display information 1311 about a time at which the biopsy was performed.

According to the present exemplary embodiment, the medical image display apparatus 300 may rapidly and accurately match the first medical image data with the second medical image data by matching the reference points of the first medical image data with the second medical image data. The medical image display apparatus 300 may display the first medical image 1320 and the second medical image 1310 of a same cross-section of the object, based on a result of the match. A user may compare the first medical image 1320 and the second medical image 1310 on which the tissue extraction positions 1325 and 1315 are marked, thereby checking a change in positions with respect to the biopsies.

FIG. 13 illustrates the example in which medical images from different times are separately displayed. However, the present exemplary embodiment is not limited thereto. For example, because the medical image display apparatus 300 has position information about a tissue extraction position, the position information being relative to a reference point, the medical image display apparatus 300 may mark tissue extraction positions with respect to different times on one medical image. The medical image display apparatus 300 may generate, from the first medical image data, a first medical image on which the tissue extraction position is marked, and may overlap and mark the tissue extraction position and a previous tissue extraction position on the first medical image. A user may compare the tissue extraction positions marked on one medical image, thereby checking a change in positions with respect to biopsies.

The medical image display apparatus 300 provides information about biopsies from different times, so that a user may easily recognize a change in tissue of an object and positions at which a biopsy was performed. Thus, according to the one or more exemplary embodiments, efficiency of the biopsy may be increased, and a follow-up with respect to past biopsies may become easy.

The medical image display apparatus 300 may be included in a general ultrasound diagnosis apparatus or may be connected to the general ultrasound diagnosis apparatus in a wired or wireless manner.

Figure 14:
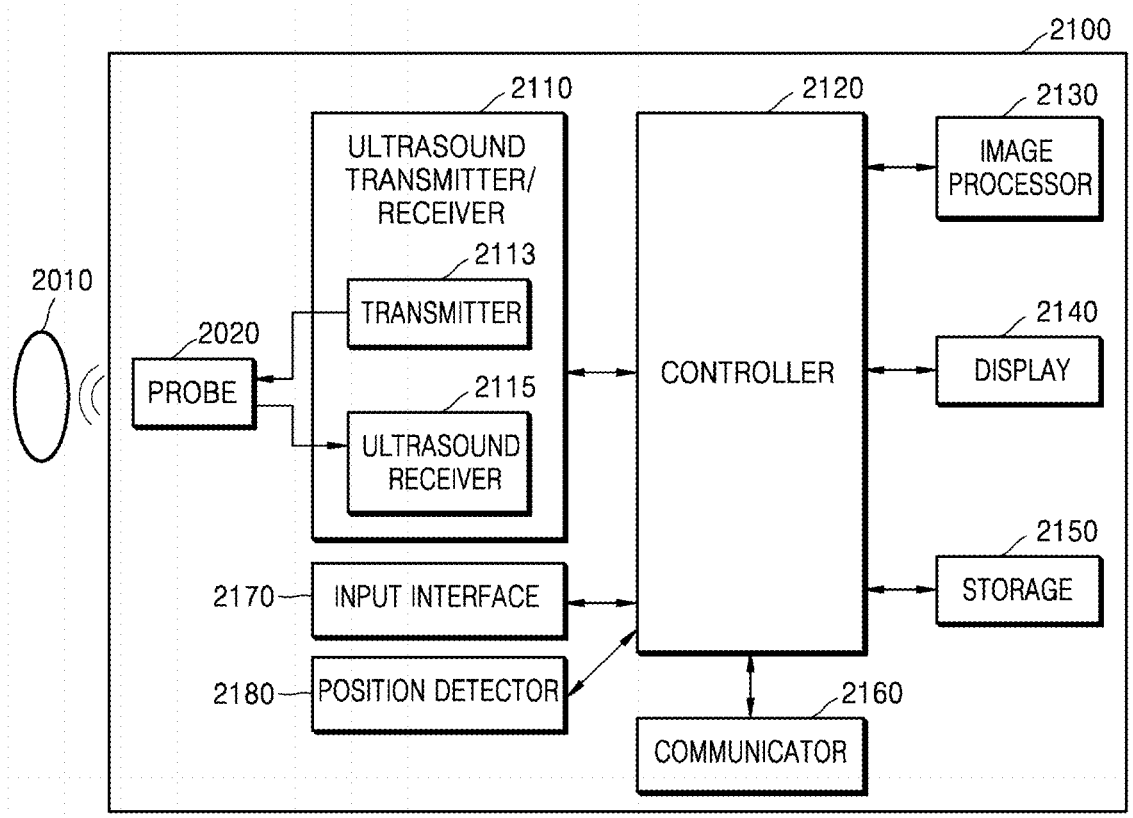
FIG. 14 is a block diagram illustrating a configuration of an ultrasound diagnosis apparatus, according to an exemplary embodiment.

FIG. 14 is a block diagram illustrating a configuration of an ultrasound diagnosis apparatus 100, i.e., a diagnostic apparatus, according to an exemplary embodiment. Referring to FIG. 14, the ultrasound diagnosis apparatus 2100 may include a probe 2020, an ultrasound transceiver 2110, a controller 2120, an image processor 2130, one or more displays 2140, a storage 2150, for example a memory, a communicator 2160, for example a communication device or an interface, and an input interface 2170.

The ultrasound diagnosis apparatus 2100 may further include a position detector 2180. The controller 2120, the one or more displays 2140, the input interface 2170, the probe 2020, the position detector 2180, and the storage 2150 may respectively correspond to the processor 310, the display 320, the input interface 330, the probe 340, the position detector 350, and the storage 360. Redundant descriptions thereof are omitted here.

The ultrasound diagnosis apparatus 2100 may be of a cart-type or a portable-type ultrasound diagnosis apparatus, that is portable, moveable, mobile, or hand-held. Examples of the portable-type ultrasound diagnosis apparatus 2100 may include a smart phone, a laptop computer, a personal digital assistant (PDA), and a tablet personal computer (PC), each of which may include a probe and a software application, but exemplary embodiments are not limited thereto.

The probe 2020 may include a plurality of transducers. The plurality of transducers may transmit ultrasound signals to an object 2010 in response to transmitting signals received by the probe 2020, from a transmitter 2113. The plurality of transducers may receive ultrasound signals reflected from the object 2010 to generate reception signals. In addition, the probe 2020 and the ultrasound diagnosis apparatus 2100 may be in one body for example disposed in a single housing, or the probe 2020 and the ultrasound diagnosis apparatus 2100 may be separate, for example disposed separately in separate housings, but linked wirelessly or via wires. In addition, the ultrasound diagnosis apparatus 2100 may include one or more probes 2020 according to exemplary embodiments.

A needle for a biopsy may be attached to the probe 2020. At least one of the needle and the probe 2020 may include a position sensor. The position detector 2180 may detect a position of at least one of the needle and the probe 2020 to which the needle is attached. The position detector 2180 may determine the position of at least one of the needle and the probe 2020 to which the needle is attached, based on information received from the position sensor included in at least one of the needle and the probe 2020 to which the needle is attached.

The controller 2120 may control the transmitter 2113 for the transmitter 2113 to generate transmitting signals to be applied to each of the plurality of transducers based on a position and a focal point of the plurality of transducers included in the probe 2020.

The controller 2120 may control the ultrasound receiver 2115 to generate ultrasound data by converting reception signals received from the probe 2020 from analogue to digital signals and summing the reception signals converted into digital form, based on a position and a focal point of the plurality of transducers.

The image processor 2130 may generate an ultrasound image by using ultrasound data generated from the ultrasound receiver 2115.

The display 2140 may display a generated ultrasound image and various pieces of information processed by the ultrasound diagnosis apparatus 2100. The ultrasound diagnosis apparatus 2100 may include two or more displays 2140 according to the present exemplary embodiment. The display 2140 may include a touch screen in combination with a touch panel.

The controller 2120 may control the operations of the ultrasound diagnosis apparatus 2100 and flow of signals between the internal elements of the ultrasound diagnosis apparatus 2100. The controller 2120 may include a memory for storing a program or data to perform functions of the ultrasound diagnosis apparatus 2100 and a processor and/or a microprocessor for processing the program or data. For example, the controller 2120 may control the operation of the ultrasound diagnosis apparatus 2100 by receiving a control signal from the input interface 2170 or an external apparatus.

The ultrasound diagnosis apparatus 2100 may include the communicator 2160 and may be connected to external apparatuses, for example, servers, medical apparatuses, and portable devices such as smart phones, tablet personal computers (PCs), wearable devices, etc., via the communicator 2160.

The communicator 2160 may include at least one element capable of communicating with the external apparatuses. For example, the communicator 2160 may include at least one among a short-range communication module, a wired communication module, and a wireless communication module.

The communicator 2160 may receive a control signal and data from an external apparatus and transmit the received control signal to the controller 2120 so that the controller 2120 may control the ultrasound diagnosis apparatus 2100 in response to the received control signal.

The controller 2120 may transmit a control signal to the external apparatus via the communicator 2160 so that the external apparatus may be controlled in response to the control signal of the controller 2120.

For example, the external apparatus connected to the ultrasound diagnosis apparatus 2100 may process the data of the external apparatus in response to the control signal of the controller 2120 received via the communicator 2160.

A program for controlling the ultrasound diagnosis apparatus 2100 may be installed in the external apparatus. The program may include command languages to perform part of operation of the controller 2120 or the entire operation of the controller 2120.

The program may be pre-installed in the external apparatus or may be installed by a user of the external apparatus by downloading the program from a server that provides applications. The server that provides applications may include a recording medium where the program is stored.

The storage 2150 may store various data or programs for driving and controlling the ultrasound diagnosis apparatus 2100, input and/or output ultrasound data, ultrasound images, applications, etc.

The input interface 2170 may receive a user's input to control the ultrasound diagnosis apparatus 2100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

The exemplary embodiments of the present disclosure can be written as computer programs and can be implemented in general-use digital computers that execute the programs using a computer-readable recording medium. In addition, a data structure used in exemplary embodiments of the present disclosure can be written in a computer-readable recording medium through various means. The one or more exemplary embodiments may be embodied as computer readable code/instructions on a recording medium, for example a program module to be executed in computers, which include computer-readable commands. For example, methods that are implemented as software modules or algorithms may be stored as computer readable codes or program instructions executable on a computer-readable recording medium.

The computer readable medium may include any usable recording medium that may be accessed by computers, volatile and non-volatile medium, and detachable and non-detachable medium. The computer readable medium may include, but is not limited to, magnetic storage media, for example ROM, floppy disks, hard disks, etc., optical recording media, for example CD-ROMs, or DVDs, etc. Also, the computer readable medium may include a computer storage medium and a communication medium.

The computer-readable recording media can be distributed over network coupled computer systems, and data stored in the distributed recording media, for example a program command and code, may be executed by using at least one computer.

The particular implementations shown and described herein are illustrative examples of the disclosure and are not intended to otherwise limit the scope of the disclosure in any way. For the sake of brevity, conventional electronics, control systems, software development and other functional aspects of the systems and components of the individual operating components of the systems may not be described in detail.

Throughout the specification, terms such as "unit" and "module" indicate a unit for processing at least one function or operation, wherein the unit and the module may be embodied as hardware or software or embodied by combining hardware and software.

The unit and the module may be formed so as to be in an addressable storage medium, or may be implemented by a program executable by a processor.

For example, the unit and the module may be implemented by components, such as software components, object-oriented software components, class components and task components, processes, functions, attributes, procedures, subroutines, segments of program code, drivers, firmware, microcode, circuitry, data, databases, data structures, tables, arrays, and variables.

While one or more exemplary embodiments have been described with reference to the figures, it will be understood by those of ordinary skill in the art that various changes in form and details may be made therein without departing from the spirit and scope as defined by the following claims.

What is claimed is:

1. A medical image display apparatus for displaying a medical image generated from first medical image data obtained from an object by a probe, the medical image display apparatus comprising:
    at least one processor configured to:
        obtain information about a first position, which is a reference with respect to a change in a position of a needle being attached to the probe, and a second position at which tissue from the object is extracted by the needle, based on a signal received from a sensor attached to at least one from among the probe and the needle, and
        determine a tissue extraction position in the first medical image data based on the information; and
    a display configured to display a first medical image on which the tissue extraction position is marked, the first medical image being generated from the first medical image data,
    wherein the at least one processor is further configured to generate a second medical image on which the tissue extraction position is marked from second medical image data corresponding to the object, based on a reference point corresponding to the first position in the second medical image data, wherein the second medical image is an image of a first cross section of the object corresponding to the first medical image,
    wherein the display is further configured to display the second medical image.

2. The medical image display apparatus of claim 1, wherein the at least one processor is further configured to determine the tissue extraction position in the second medical image data corresponding to the object, based on the information, and
    wherein the second medical image data comprises at least one of magnetic resonance (MR) image data, computed tomography (CT) image data, and model image data obtained by modeling the object.

3. The medical image display apparatus of claim 2, wherein the at least one processor is further configured to:
    obtain information about a position of the needle based on the signal received from the sensor attached to the at least one of the probe and the needle,
    match the position of the needle with the second medical image data, and
    determine the tissue extraction position in the second medical image data, based on a result of the matching.

4. The medical image display apparatus of claim 2, wherein the at least one processor is further configured to:
    obtain information about the first position of the needle before the tissue is extracted from the object by the needle,
    obtain information about the second position of the needle at which the tissue is extracted from the object by the needle, and
    determine the tissue extraction position to correspond to the second position in the second medical image data, based on the reference point corresponding to the first position in the second medical image data.

5. The medical image display apparatus of claim 4, further comprising an input interface,
wherein, the at least one processor is further configured to obtain the information about the first position of the needle upon receipt of a user input through the input interface, and match the first position of the needle with the reference point in the second medical image data.

6. The medical image display apparatus of claim 4, wherein the reference point is determined based on at least one from among pre-stored information or a user input.

7. The medical image display apparatus of claim 4, wherein the at least one processor is further configured to:
obtain, as the information about the second position, coordinate information corresponding to the second position in a coordinate system including the first position as a starting point, and
determine the tissue extraction position with respect to the reference point, based on the coordinate information.

8. The medical image display apparatus of claim 4, further comprising an input interface,
wherein the information about the first position and the information about the second position are obtained by a position sensor included in the probe, and
wherein the at least one processor is further configured to obtain information about a position of the probe, upon receipt of a user input via the input interface, and determine the information about the second position based on at least one of a distance which the needle has moved with respect to the probe and a direction in which the needle has moved with respect to the probe.

9. The medical image display apparatus of claim 2, further comprising a storage configured to store third medical image data corresponding to a biopsy that was previously performed on the object, the third medical image data comprising information about a previous reference point and a previous tissue extraction position,
wherein the at least one processor is further configured to:
obtain the third medical image data from the storage,
match the second medical image data with the third medical image data by matching a reference point of the second medical image data with the previous reference point of the third medical image data,
generate, from the second medical image data, a second medical image on which the tissue extraction position is marked, and
generate, from the third medical image data, a third medical image on which the previous tissue extraction position is marked, wherein the third medical image includes a cross-section of the object which corresponds to the second medical image, and
wherein the display is further configured to display the second medical image and the third medical image.

10. The medical image display apparatus of claim 4, further comprising a storage configured to store, as the information about the second position, coordinate information corresponding to the second position in a coordinate system including the first position as a starting point.

11. A method of displaying a medical image generated from first medical image data obtained from an object by a probe, the method comprising:
obtaining information about a first position, which is a reference with respect to a change in a position of a needle being attached to the probe, and a second position at which tissue from the object is extracted by the needle, based on a signal received from a sensor attached to at least one from among the probe and the needle;
determining a tissue extraction position in the first medical image data based on the information;
displaying a first medical image on which the tissue extraction position is marked, the first medical image being generated from the first medical image data;
generating a second medical image on which the tissue extraction position is marked from second medical image data corresponding to the object, based on a reference point corresponding to the first position in the second medical image data, wherein the second medical image is an image of a first cross section of the object corresponding to the first medical image; and
displaying the second medical image.

12. The method of claim 11, further comprising:
determining the tissue extraction position in the second medical image data corresponding to the object, based on the information,
wherein the second medical image data comprises at least one of magnetic resonance (MR) image data, computed tomography (CT) image data, and model image data obtained by modeling the object.

13. The method of claim 12,
wherein the obtaining of the information about the position comprises obtaining information about a position of the needle based on the signal received from the sensor attached to at least one of the probe and the needle, and
wherein the determining of the tissue extraction position comprises:
matching the position of the needle with the second medical image data; and
determining the tissue extraction position in the second medical image data, based on a result of the matching.

14. The method of claim 12,
wherein the obtaining of the information about the position comprises:
obtaining information about the first position of the needle before the tissue is extracted from the object by the needle; and
obtaining information about the second position of the needle at which the tissue is extracted from the object by the needle, and
wherein the determining of the tissue extraction position in the second medical image data comprises determining the tissue extraction position to correspond to the second position in the second medical image data, based on the reference point corresponding to the first position in the second medical image data.

15. The method of claim 14,
wherein the information about the first position of the needle is obtained when a user input is received, and
wherein the determining of the tissue extraction position in the second medical image data comprises matching a position of the needle with the second medical image data by matching the first position of the needle with the reference point in the second medical image data.

16. The method of claim 14, wherein the reference point is determined based on at least one from among pre-stored information or a user input.

17. The method of claim 14,
wherein the obtaining of the information about the second position comprises obtaining, as the information about the second position, coordinate information corresponding to the second position in a coordinate system including the first position as a starting point, and wherein the determining of the tissue extraction position in the second medical image data comprises determining the tissue extraction position with respect to the reference point, based on the coordinate information.

18. The method of claim 14,
wherein the information about the first position and the information about the second position are obtained by a position sensor included in the probe, and
wherein the obtaining of the information about the second position comprises:
obtaining, when a user input is received, information about a position of the probe to which the needle is attached; and
determining the information about the second position based on at least one of a distance which the needle has moved with respect to the probe and a direction in which the needle has moved with respect to the probe.

19. The method of claim 12, further comprising storing third medical image data in relation to a biopsy that was previously performed on the object, the third medical image data comprising information about a previous reference point and a previous tissue extraction position,
wherein the displaying of the second medical image comprises:
obtaining the stored third medical image data;
matching the second medical image data with the third medical image data by matching a reference point of the second medical image data with the previous reference point of the third medical image data;
generating, from the second medical image data, a second medical image on which the tissue extraction position is marked;
generating, from the third medical image data, a third medical image on which the previous tissue extraction position is marked, wherein the third medical image includes a cross-section of the object which corresponds to the second medical image; and
displaying the second medical image and the third medical image.

20. A non-transitory computer-readable recording medium having recorded thereon instructions to perform a method of displaying a medical image generated from first medical image data obtained from an object by a probe, the method comprising:
obtaining information about a first position, which is a reference with respect to a change in a position of a needle being attached to the probe, and a second position at which tissue from the object is extracted by the needle, based on a signal received from a sensor attached to at least one from among the probe and the needle;
determining a tissue extraction position in the first medical image data based on the information;
displaying a first medical image on which the tissue extraction position is marked, the first medical image being generated from the first medical image data, wherein the needle is attached to the probe and the sensor is attached to at least one from among the probe and the needle;
generating a second medical image on which the tissue extraction position is marked from second medical image data corresponding to the object, based on a reference point corresponding to the first position in the second medical image data, wherein the second medical image is an image of a first cross section of the object corresponding to the first medical image; and
displaying the second medical image.

* * * * *